United States Patent
Ni

(10) Patent No.: US 10,980,741 B2
(45) Date of Patent: *Apr. 20, 2021

(54) COMPOSITIONS AND METHODS FOR TREATING PTERYGIUM RECURRENCE

(71) Applicant: Cloudbreak Therapeutics, LLC, Irvine, CA (US)

(72) Inventor: Jinsong Ni, Irvine, CA (US)

(73) Assignee: Cloudbreak Therapeutics, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/210,896

(22) Filed: Dec. 5, 2018

(65) Prior Publication Data

US 2019/0110984 A1 Apr. 18, 2019

Related U.S. Application Data

(63) Continuation of application No. 15/991,698, filed on May 29, 2018, now Pat. No. 10,149,820, which is a continuation of application No. 15/474,620, filed on Mar. 30, 2017, now Pat. No. 9,987,223, which is a continuation of application No. 15/375,820, filed on Dec. 12, 2016, now Pat. No. 9,980,901, which is a continuation of application No. PCT/US2016/035726, filed on Jun. 3, 2016.

(60) Provisional application No. 62/172,063, filed on Jun. 6, 2015, provisional application No. 62/186,660, filed on Jun. 30, 2015.

(51) Int. Cl.

| | | |
|---|---|---|
| *A61P 27/02* | (2006.01) | |
| *A61K 31/496* | (2006.01) | |
| *A61K 9/00* | (2006.01) | |
| *A61F 9/00* | (2006.01) | |
| *A61K 45/06* | (2006.01) | |
| *A61K 47/26* | (2006.01) | |
| *A61K 9/06* | (2006.01) | |
| *A61K 9/08* | (2006.01) | |
| *A61K 9/10* | (2006.01) | |
| *A61K 9/107* | (2006.01) | |
| *A61K 31/404* | (2006.01) | |
| *A61K 31/407* | (2006.01) | |
| *A61P 27/00* | (2006.01) | |

(52) U.S. Cl.
CPC ............ *A61K 9/0048* (2013.01); *A61F 9/00* (2013.01); *A61F 9/0017* (2013.01); *A61K 9/0051* (2013.01); *A61K 9/06* (2013.01); *A61K 9/08* (2013.01); *A61K 9/10* (2013.01); *A61K 9/107* (2013.01); *A61K 31/404* (2013.01); *A61K 31/407* (2013.01); *A61K 31/496* (2013.01); *A61K 45/06* (2013.01); *A61K 47/26* (2013.01); *A61P 27/00* (2018.01); *A61P 27/02* (2018.01)

(58) Field of Classification Search
CPC .. A61K 9/0048; A61K 31/496; A61K 9/0051; A61P 27/02; A61F 9/00
See application file for complete search history.

(56) References Cited

U.S. PATENT DOCUMENTS

| | | | |
|---|---|---|---|
| 8,747,852 B1 | 6/2014 | Pham | |
| 9,980,901 B2 | 5/2018 | Ni | |
| 9,987,223 B2 | 6/2018 | Ni | |
| 10,149,820 B2* | 12/2018 | Ni | A61K 9/0051 |
| 10,335,408 B2 | 7/2019 | Ni et al. | |
| 10,688,092 B2 | 6/2020 | Ni | |
| 2008/0003219 A1 | 1/2008 | Peyman | |
| 2012/0315282 A1 | 12/2012 | Bedinger et al. | |
| 2013/0012531 A1* | 1/2013 | King | A61P 27/02 514/275 |
| 2013/0316006 A1 | 11/2013 | Popov et al. | |
| 2013/0324481 A1 | 12/2013 | Wong et al. | |
| 2014/0128395 A1 | 5/2014 | Ferrari | |
| 2014/0186336 A1 | 7/2014 | Pham | |
| 2014/0235678 A1 | 8/2014 | Böttger et al. | |
| 2015/0037422 A1 | 2/2015 | Kaplan et al. | |
| 2015/0038905 A1* | 2/2015 | Andino | A61M 5/347 604/117 |
| 2015/0164790 A1 | 6/2015 | Bottger et al. | |
| 2015/0258120 A1 | 9/2015 | Zarnitsyn et al. | |
| 2015/0265469 A1 | 9/2015 | Olson | |
| 2016/0038760 A1 | 2/2016 | Hamrah et al. | |
| 2017/0020729 A1 | 1/2017 | Jarrett | |
| 2017/0172915 A1 | 6/2017 | Ni | |
| 2017/0209368 A1 | 7/2017 | Ni | |
| 2018/0271780 A1 | 9/2018 | Ni | |
| 2018/0271871 A1 | 9/2018 | Van Voorhis et al. | |
| 2019/0015409 A1 | 1/2019 | Ni | |
| 2019/0290643 A1 | 9/2019 | Ni | |
| 2020/0323844 A1 | 10/2020 | Ni | |

FOREIGN PATENT DOCUMENTS

| | | |
|---|---|---|
| CN | 1247469 | 3/2000 |
| CN | 100455568 | 1/2009 |
| CN | 102018686 | 4/2011 |
| CN | 103212075 | 7/2013 |
| CN | 103764118 | 4/2014 |

(Continued)

OTHER PUBLICATIONS

CAS Registry record for Nintedanib, retrieved from STN on Aug. 12, 2020. (Year: 2020).*

"Concise Description of Relevance of International Patent Application Publication No. WO 2007/038453 to Pending Claims of U.S. Appl. No. 15/474,620," Third-Party Submission Under 37 CRF 1.290 in U.S. Appl. No. 15/474,620, dated Oct. 20, 2017, 9 pages.

(Continued)

*Primary Examiner* — Theodore R. West

(74) *Attorney, Agent, or Firm* — Fish & Richardson P.C.

(57) ABSTRACT

Compositions and methods for inducing pterygium regression from visual axis/central cornea, stabilizing pterygium, treating hyperemia and symptoms in pterygium patients, and treating pterygium recurrence following pterygiectomy are disclosed. The methods include administration of a multikinase inhibitor, an antimetabolite or a combination thereof to patients in need thereof.

19 Claims, 5 Drawing Sheets

(56) References Cited

FOREIGN PATENT DOCUMENTS

| CN | 103889399 | 6/2014 |
|---|---|---|
| CN | 103998431 | 8/2014 |
| CN | 104379128 | 2/2015 |
| CN | 104379129 | 2/2015 |
| CN | 104379133 | 2/2015 |
| CN | 104448300 | 3/2015 |
| RU | 2351298 | 4/2009 |
| WO | WO 2007/038453 | 4/2007 |
| WO | WO 2012/167143 | 12/2012 |
| WO | WO 2013/188283 | 12/2013 |
| WO | WO 2014/074823 | 5/2014 |
| WO | WO 2016/029191 | 2/2016 |
| WO | WO 2016/209555 | 12/2016 |
| WO | WO 2017/210130 | 12/2017 |
| WO | WO 2018/022437 | 2/2018 |

OTHER PUBLICATIONS

"Concise Description of Relevance of International Patent Application Publication No. WO 2013/188283 to Pending Claims of U.S. Appl. No. 15/474,620," Third-Party Submission Under 37 CRF 1.290 in U.S. Appl. No. 15/474,620, dated Oct. 20, 2017, 8 pages.
"Concise Description of Relevance of International Patent Application Publication No. WO 2016/209555 to Pending Claims of U.S. Appl. No. 15/474,620," Third-Party Submission Under 37 CRF 1.290 in U.S. Appl. No. 15/474,620, dated Oct. 20, 2017, 10 pages.
"Concise Description of Relevance of Roskoski, Biochemical and Biophysical Research Communications 356 (2007) 323-328 to Pending Claims of U.S. Appl. No. 15/474,620," Third-Party Submission Under 37 CRF 1.290 in U.S. Appl. No. 15/474,620, dated Oct. 20, 2017, 2 pages.
"Concise Description of Relevance of Roth et al. J. Med. Chem. (2015) 58, 1053-1063 to Pending Claims of U.S. Appl. No. 15/474,620," Third-Party Submission Under 37 CRF 1.290 in U.S. Appl. No. 15/474,620, dated Oct. 20, 2017, 2 pages.
"Third Party Pre-Issuance Submission Pursuant to 35 U.S.C. § 122(e) and 37 C.F.R. §1.290 for U.S. Appl. No. 15/474,620," Third-Party Submission Under 37 CRF 1.290 in U.S. Appl. No. 15/474,620, dated Oct. 20, 2017, 3 pages.
"Third-Party Submission Under 37 CFR 1.290 Concise Description of Relevance, for U.S. Appl. No. 15/474,620," Third-Party Submission Under 37 CRF 1.290 in U.S. Appl. No. 15/474,620, dated Oct. 20, 2017, 4 pages.
Al-Torbak, "Photodynamic Therapy with Verteporfin for Corneal Neovascularization," Middle East Afr. J. Opthalmol., Apr.-Jun. 2012, 19(2):185-189.
Amoozgar et al., "A role for antimetabolites in glaucoma tube surgery: current evidence and future directions.", Curr Opin Ophthalmol., 27(2): 164-9, 2016.
Amparo et al, "Safety and Efficacy of the Multitargeted Receptor Kinase Inhibitor Pazopanib in the Treatment of Corneal Neovascularization," Investigative Ophthalmology & Visual Science, Jan. 2013, 54(1):537-544.
Avastin® Label, Revised Sep. 2011.
Aversa et al., "Linifanib: current status and future potential in cancer therapy", Expert Rev. Anticancer Ther. Early online, 1-11, 2015.
Bayyoud et al., "Cytotoxic Properties of Sunitinib and Sorafenib on Human Corneal Epithelial Cells," Current Eye Research, 2014, 39(2):149-154.
Bhartiya et al., "The Need to maintain Intraocular Pressure over 24 Hours", Journal of Current Glaucoma Practice, 6(3): 120-123, 2012.
Brandão et al., "Update on Minimally Invasive Glaucoma Surgery (MIGS) and New Implants", Journal of Ophthalmology, 12 pages, 2013.
Chaudhary et al., "XEN Gel Implant: a new surgical approach in glaucoma", Expert Review of Medical Devices, 15:1, 47-59, 2018.
Cox et al., "Doxycycline's Effect on Ocular Angiogenesis: an In Vivo Analysis," Ophthalmology, Sep. 2010; 117(9):1782-91.

Daniels et al., "Imatinib Treatment for Idiopathic Pulmonary Fibrosis Randomized Placebo-controlled Trial Results", J Respir Crit Care Med vol. 181. pp. 604-610, 2010.
Extended European Search Report in Application No. 16808064.6, dated Jan. 3, 2019.
Fossarello et al., "Photodynamic Therapy of Corneal Neovascularization with Verteporfin," Cornea, Jul. 1, 2003, 22(5):485-488.
Fossarello et al., "Photodynamic Therapy of Pterygium With Verteporfin: A Preliminary Report," Cornea, May 2004, 23(4): 330-338.
Gedde et al., "Treatment Outcomes in the Tube Versus Trabeculectomy (TVT) Study After Five Years of Follow-up", Am J Ophthalmol., 153(5): 789-803, 2012.
Hall et al., "Angiogenesis inhibition as a therapeutic strategy in non-small cell lung cancer (NSCLC)," Transl Lung Cancer Res., Oct. 2015;4(5), 515-23.
Hilberg et al, "BIBF 1120: Triple Angiokinase Inhibitor with Sustained Receptor Blockade and Good Antitumor Efficacy," Cancer Res., Jun. 15, 2008; 68(12):4774-4782.
Hojjat-Farsangi, "Small-Molecule Inhibitors of the Receptor Tyrosine Kinases Promising Tools for Targeted Cancer Therapies", Int. J. Mol. Sci., 15, 13768-13801, 2014.
Hostettler et al., "Anti-fibrotic effects of nintedanib in lung fibroblasts derived from patients with idiopathic pulmonary fibrosis," Respiratory research, 2014, 15:157.
Hueber et al., "Photodynamic therapy for wound-healing modulation in pterygium surgery. A clinical pilot study," Graefe's Arch Clin Exp Opthalmol, Apr. 2005, 243:942-946.
Huu et al, "Light-responsive nanoparticle depot to control release of a small molecule angiogenesis inhibitor In the posterior segment of the eye" Journal of Controlled Release, Feb. 28, 2015, 200:71-77.
International Preliminary Report on Patentability in International Application No. PCT/US16/35726, dated Dec. 21, 2017, 10 pages.
International Search Report and Written Opinion in Application No. PCT/US17/34792, dated Oct. 25, 2017, 14 pages.
International Search Report and Written Opinion in International Application No. PCT/US16/35726, dated Sep. 1, 2016, 13 pages.
International Search Report and Written Opinion in International Application No. PCT/US17/34795, dated Aug. 27, 2017, 10 pages.
Jovanovic et al., "The Effect of Topical Doxycycline on Corneal Neovascularization," Current Eye Research, Feb. 1, 2014, 39(2):142-148.
Kaplowitz et al., "Techniques and Outcomes of Minimally-Invasive Trabecular Ablation and Bypass Surgery",Br J Ophthalmol., 98(5): 579-585, 2014.
Kareem et al, The use of antimetabolites as adjunctive therapy in the surgical treatment of pterygium Clinical Ophthalmology, vol. 6 (Nov. 7, 2012), 6 pages.
Katoh, "FGFR inhibitors: Effects on cancer cells, tumor microenvironment and whole-body homeostasis (Review)", International Journal of Molecular Medicine 38: 3-15, 2016.
Kay et al., "Imatinib Mesylate Treatment of Nephrogenic Systemic Fibrosis", Arthritis & Rheumatism, vol. 58, No. 8, pp. 2543-2548, 2008.
Kitagawa et al., "Activity-based kinase profiling of approved tyrosine kinase inhibitors", Genes to Cells, 18, 110-122, 2013.
Ko et al., "Inhibition of Corneal Neovascularization by Subconjunctival and Topical Bevacizumab and Sunitinib in a Rabbit Model," Cornea, May 2013;32(5):689-695.
Kumar et al, "Myelosuppression and kinase selectivity of multikinase angiogenesis inhibitors," British Journal of Cancer, Oct. 2009; 101:1717-1723.
Lee et al., "Effect of porcine chondrocyte-derived extracellular matrix on the pterygium in mouse model," Graefes Arch Clin Exp Ophthalmol., Apr. 2014; 252(4):609-618.
Lee et al., "Pivotal role of vascular endothelial growth factor pathway in tumor angiogenesis", ASTR, 8 pages, 2015.
Lucentis® Label, Clinical Trial Date Dec. 2011.
Maddula et al, "Horizons in Therapy for Corneal Angiogenesis," Ophthalmology, Mar. 2011, 118(3):591-599.
OFEV Capsules Approval Letter, Application No. 205832Orig1s000, 8 pages, Approval date Oct. 15, 2014.
Ornitz et al., "The Fibroblast Growth Factor signaling pathway", WIREs Dev Biol., vol. 4, 215-266, 2015.

(56) References Cited

OTHER PUBLICATIONS

Perez-Santonja et al., "Inhibition of Corneal Neovascularization by Topical Bevacizumab (Anti-VEGF) and Sunitinib (Anti-VEGF and Anti-PDGF) in an Animal Model," Am J Ophthalmol., Oct. 2010;150(4):519-528.
Pozarowska et al., "The era of anti-vascular endothelial growth factor (VEGF) drugs in ophthalmology, VEGF and anti-VEGF therapy", Cent. Eur. J. Immunol., 41(3): 311-316, 2016.
Roskoski Jr., "Sunitinib: A VEGF and PDGF receptor protein kinase and angiogenesis inhibitor," Biochem. Biophys. Res. Comm. (2007) 356:323-328.
Roth et al. "Nintedanib: From Discovery to the Clinic" J. Med. Chem (2015) 58:1053-1063.
Rúa et al., "Oral Doxycycline Reduces Pterygium Lesions; Results from a Double Blind, Randomized, Placebo Controlled Clinical Trial," PLOS ONE, Dec. 2012, 7(12):e52696, 7 pages.
Schlunck et al., "Conjunctival fibrosis following filtering glaucoma surgery.", Exp Eye Res., 142: 76-82, 2016.
Sonoda et al., "ACAID induced by allogeneic corneal tissue promotes subsequent survival of orthotopic corneal grafts.", Invest Ophthalmol Vis Sci., 41(3): 790-8, 2000.
Sonoda et al., "Characterization of cell-mediated immune responses elicited by orthotopic corneal allografts in mice.", Invest Ophthalmol Vis Sci., 36(2): 427-34, 1995.
Third Party Submission Under 37 CFR 1.290 for U.S. Appl. No. 15/474,620, dated Oct. 20, 2017, 3 pages.
U.S. Appl. No. 62/183,180, filed Jun. 22, 2015, 14 pages.
Van Bergen et al., "Inhibition of placental growth factor improves surgical outcome of glaucoma surgery.", J Cell Mol Med., 17(12): 1632-43, 2013.
Vandewalle et al., "Intracameral bevacizumab as an adjunct to trabeculectomy: a 1-year prospective, randomised study.", Br J Ophthalmol., 98(1): 1-6, 2013.
Wollin et al., "Mode of action of nintedanib in the treatment of idiopathic pulmonary fibrosis," Eur. Respir. J., 2015, 45(5):1434-45.
Wong et al., "Matrix metalloproteinase inhibition modulates postoperative scarring after experimental glaucoma filtration surgery.", Invest Ophthalmol Vis Sci., 44(3): 1097-1103, 2003.
Yamagami et al., "The critical role of lymph nodes in corneal alloimmunization and graft rejection.", Invest Ophthalmol Vis Sci., 42(6): 1293-8, 2001.
Yu et al., "High-risk corneal allografts: A therapeutic challenge.", World J Transplant., 6(1): 10-27, 2016.
Chinese Office Action in Chinese Appln. No. 201680042858, dated Oct. 21, 2019. 12 pages (with English translation).
Kria, "Growth factors in cultured pterygium fibroblasts: immunohistochemical and ELISA analysis," Graefe's Arch for Clin. Exp. Ophthalmol., 1998, 236:702-708.
Kria, "Immunohistochemical localization of basic fibroblast growth factro, platelet derived growth factor, transforming growth factor-beta and tumor necrosis factor-a in the pterygium," Acta Histochem, 1996, 98:195-201.
Peng, "Vascular endothelial growth factor gene polymorphism and protein expression in pathogenesis of pterygium," Br J Ophthalmol., 2013, 98:556-561.
Zhang et al., "Correlation of vascular endothelial growth factor and CD105-microvascular density in primary pterygium," J Huazhong Univ Sci Technol., 2011, 31(4):560-564.
Masoumpour et al., "Current and future techniques in wound healing modulation after glaucoma filtering surgeries," The Open Ophthalmology Journal, 2016, 10(1):68-85.
Supplementary European Search Report in EP Appln. No. 17807295, dated Jan. 29, 2020, 7 pages.
Extended European Search Report in Application No. 16808064.6, dated Jan. 3, 2019, 8 pages.
Livezeanu et al., "Angiogenesis in the pathogenesis of pterygium", Rom. J. Morph. Embryol, Jan. 2011, pp. 837-844.

[No Author Listed], "Clinical Pharmacology and Biopharmaceutics Review(s)," Center for Drug Evaluation and Research, submitted by Boehringer Ingelheim, Inc. on May 2, 2014, 140 pages (Exhibit No. 1026).
[No Author Listed], "EPAR Summary for the Public: Vargatef (nintedanib)," European Medicines Agency, © 2015, 3 pages (Exhibit No. 1013).
[No Author Listed], "OFEV (nintedanib) FDA Label," Boehringer Ingelheim Pharmaceuticals, Inc., © 2014, 18 pages (Exhibit No. 1012).
[No Author Listed], "Standard Affidavit," Internet Archive Standard Affidavit, 2020, 2 pages. retrieved from URL: https://archive.org/legal/affidavit/php, retrieved on Jul. 31, 2020 (Exhibit No. 1029).
[No Author Listed], "Table of Contents," IOVS, 2013, 54(1):1-24, retrieved from URL: https://web.archive.org/web/20131008205602/http:/www.iovs.org/content/54/1.toc, retrieved on Jul. 30, 2020 (Exhibit No. 1028).
Affidavit of Elizabeth Rosenberg, dated Aug. 5, 2020, 22 pages (Exhibit No. 1030).
*Allgenesis Biotherapeutics Inc. v. Cloudbreak Therapeutics, LLC*, "Declaration of Dr. Thomas Malone," Case No. IPR2020-01438, U.S. Pat. No. 10,149,820, dated Aug. 7, 2020, 113 pages (Exhibit No. 1005).
*Allgenesis Biotherapeutics Inc. v. Cloudbreak Therapeutics, LLC*, "Declaration of Patrick Gordis," Case No. IPR2020-01438, U.S. Pat. No. 10,149,820, dated Aug. 6, 2020, 21 pages (Exhibit No. 1027).
*Allgenesis Biotherapeutics Inc. v. Cloudbreak Therapeutics, LLC*, "Petition for Inter Partes Review of U.S. Pat. No. 10,149,820," Case No. IPR2020-01438, U.S. Pat. No. 10,149,820, dated Aug. 7, 2020, 81 pages.
*Allgenesis Biotherapeutics Inc. v. Cloudbreak Therapeutics, LLC*, "Petitioner's Power of Attorney," Case No. IPR220-01438, U.S. Pat. No. 10,149,820, dated Aug. 7, 2020, 5 pages.
Amparo et al, "Safety and Efficacy of the Multitargeted Receptor Kinase Inhibitor Pazopanib in the Treatment of Corneal Neovascularization," Investigative Ophthalmology & Visual Science, Jan. 2013, 54(1):537-544 (Exhibit No. 1009).
Davis et al., "Comprehensive analysis of kinase inhibitor selectivity," Nature Biotechnology, 2011, 29(11):1046-1051 (Exhibition No. 1016).
Gougis et al., "Clinical pharmacology of anti-angiogenic drugs in oncology," Critical Reviews in Oncology/Hematology, 2017, 119:75-93 (Exhibit No. 1024).
Gover-Proaktor et al., "Bosutinib, dasatinib, imatinib, nilotinib, and ponatinib differentially affect the vascular molecular pathways and functionality of human endothelial cells," Leukemia & Lymphoma, 2018, 60:189-199 (Exhibit No. 1022).
Inventor Declaration filed during the Prosecution of U.S. Appl. No. 20130012531 to King et al., dated Sep. 2012, 3 pages (Exhibit No. 1020).
Manallack et al., "The significance of acid/base properties in drug discovery," Chem. Soc. Rev., 2013, 42:485-496 (Exhibit No. 1018).
Memorandum from Deputy Commissioner from Patent Examination Policy to Patent Examining Corps, dated Apr. 5, 2018, 7 pages (Exhibit No. 1019).
PCT International Publication No. WO 2007038453, published on Apr. 5, 2007, Peyman et al., 54 pages (Exhibit No. 1010).
PCT International Publication No. WO 2016209555, published on Dec. 29, 2016, Nguyen et al., 42 pages (Exhibit No. 1006).
Perez-Santonja et al., "Inhibition of Corneal Neovascularization by Topical Bevacizumab (Anti-VEGF) and Sunitinib (Anti-VEGF and Anti-PDGF) in an Animal Model," Am J Ophthalmol., Oct. 2010, 150(4):519-528 (Exhibit No. 1014).
Prosecution History of U.S. Pat. No. 10,149,820, filed on May 29, 2018, 132 pages (Exhibit No. 1002).
Prosecution History of U.S. Pat. No. 10,154,994, filed on Sep. 11, 2017, 709 pages (Exhibit No. 1015).
Prosecution History of U.S. Pat. No. 9,987,223, filed on Apr. 11, 2017, 562 pages (Exhibit No. 1025).
Response to Office Action in U.S. Appl. No. 16/210,896, filed Apr. 10, 2020, 20 pages (Exhibit No. 1023).

(56) References Cited

OTHER PUBLICATIONS

Roskoski Jr., "Classification of small molecule protein kinase inhibitors based upon the structures of their drug-enzyme complexes," Pharmacological Research, 2016, 103:26-48 (Exhibit No. 1017).

Roth et al., "Nintedanib: From Discovery to the Clinic," J. Med. Chem., 2015, 58:1053-1063 (Exhibit No. 1011).

U.S. Appl. No. 2008/0003219, published on Jan. 3, 2008, Peyman, 11 pages (Exhibit No. 1021).

U.S. Appl. No. 2013/0012531, published on Jan. 10, 2013, King et al., 13 pages (Exhibit No. 1008).

U.S. Pat. No. 10,149,820, issued on Dec. 11, 2018, Ni, 20 pages (Exhibit No. 1001).

U.S. Appl. No. 62/172,063, filed Jun. 6, 2015, 18 pages (Exhibit No. 1003).

U.S. Appl. No. 62/183,180, filed Jun. 22, 2015, 24 pages (Exhibit No. 1007).

U.S. Appl. No. 62/186,660, filed Jun. 30, 2015, 20 pages (Exhibit No. 1004).

\* cited by examiner

US 10,980,741 B2

COMPOSITIONS AND METHODS FOR TREATING PTERYGIUM RECURRENCE

CLAIM OF PRIORITY

This application is a continuation of U.S. application Ser. No. 15/991,698, filed May 29, 2018, which is a continuation of U.S. application Ser. No. 15/474,620, filed Mar. 30, 2017, which is a continuation of U.S. application Ser. No. 15/375,820, filed Dec. 12, 2016, which is a continuation application of International Application No. PCT/US2016/035726, filed on Jun. 3, 2016, which claims the benefit of U.S. Provisional Patent Application Ser. No. 62/172,063, filed on Jun. 6, 2015 and U.S. Provisional Patent Application Ser. No. 62/186,660, filed on Jun. 30, 2015, the entire contents of each are hereby incorporated by reference.

TECHNICAL FIELD

The present disclosure relates to ocular compositions and methods for treating primary and recurrent pterygium, and more particularly to compositions and methods for inducing pterygium regression from visual axis/central cornea, stabilize pterygium, reducing ocular hyperemia and pterygium recurrence prior to, in conjunction with or following pterygium surgery.

BACKGROUND

Pterygium is an ocular surface disease, where an abnormal epithelial and fibroblast growth extends from the nasal or temporal conjunctiva across the limbus onto the cornea. Pterygium patients often experience symptoms of ocular discomfort, hyperemia, and are at risk of visual impairment if the lesion encroaches on the visual axis.

SUMMARY

In certain aspects, the disclosure provides a method for treating primary and recurrent pterygium by administering (1) a multikinase inhibitor, (2) an antimetabolite or (3) a combination of a multikinase inhibitor and an antimetabolite to the eye of a subject in need of such treatment. In certain aspect, the disclosed methods stabilize pterygium and prevent further growth of the diseased tissue. In another aspect, the disclosed methods induce pterygium regression from visual axis/central cornea. In certain aspect, the disclosed multikinase inhibitor targets kinase receptors of VEGFR (1, 2, 3) and PDGFR ($\alpha$, $\beta$). In certain aspect, the multikinase inhibitor is in a topical ocular formulation administered topically to the affected eye. In certain aspect, the topical ocular formulation is a solution, a suspension or an emulsion. In another aspect, the multikinase inhibitor is in an implant or semi-solid sustained release formulation injected into the affected eye. In certain aspect, the antimetabolites are Mitomycin C, 5-Fluorouracil and Thiotepa. In certain aspect, the antimetabolite is in a topical ocular formulation administered topically to the affected eye. In certain aspect, the topical ocular formulation is a solution, a suspension or an emulsion. In another aspect, the antimetabolite is in an implant or semi-solid sustained release formulation injected into the affected eye. In certain aspect, the disclosed methods are performed by the combination of a multikinase inhibitor and an antimetabolite. In certain aspect, the combination of a multikinase inhibitor and an antimetabolite is in a topical ocular formulation administered topically to the affected eye. In certain aspect, the topical ocular formulation is a solution, a suspension or an emulsion. In another aspect, the combination of a multikinase inhibitor and an antimetabolite is in an implant or semi-solid sustained release formulation injected into the affected eye. In certain aspect, the disclosed methods reduce hyperemia, abnormal neovascularization and other symptoms in pterygium patients. In another aspect, the disclosed methods prevent pterygium recurrence following pterygium surgery. In certain aspect, the disclosed methods are performed before surgical removal of pterygium, in conjunction with surgery for pterygium removal or after surgical removal of pterygium, to reduce or prevent pterygium recurrence. In certain aspect, the disclosed multikinase inhibitor targets minimum kinase receptors of VEGFR (1, 2, 3), PDGFR ($\alpha$, $\beta$), FGFR (1, 2, 3, 4) and optimal kinase receptors of FLT3, Lck, Lyn and Src as additional. In certain aspect, the disclosed multikinase inhibitor is nintedanib. In certain aspect, the disclosed methods use a topical ocular formulation. In certain aspect, the formulation is an aqueous solution, a suspension or an emulsion. In certain aspect, the concentration of nintedanib in the formulation is from 0.001% to 10%. In certain aspect, the formulation is an implant or semi-solid sustained release formulation injected into the affected eye. In certain aspect, the amount of nintedanib in the implant is from 1 µg to 100 mg.

In one aspect, the disclosure provides for a method for inducing pterygium regression from visual axis/central cornea, including administering to an affected eye of a subject in need of such treatment a therapeutically effective amount of (1) a multikinase inhibitor; (2) an antimetabolite that blocks epithelial and fibroblast cell proliferation; or (3) a combination thereof. In some embodiments of all aspects, the administration of the multikinase inhibitor, the antimetabolite, or combination thereof results in a decrease of the pterygium size in the affected eye. In some instances, the administration of the multikinase inhibitor, the antimetabolite, or combination thereof results in a negative pterygium growth rate in the affected eye.

In another aspect, the disclosure provides for a method for stabilizing pterygium, including administering to an affected eye of a subject in need of such treatment a therapeutically effective amount of (1) a multikinase inhibitor; (2) an antimetabolite that blocks epithelial and fibroblast cell proliferation; or (3) a combination thereof. In some cases, the administration of the multikinase inhibitor, the antimetabolite, or combination thereof results in stabilization of the pterygium size in the affected eye. In some instances, the administration of the multikinase inhibitor, the antimetabolite, or combination thereof results in an about zero pterygium growth rate in the affected eye.

In some embodiments of all aspects, the multikinase inhibitor reduces the activity of one or more intracellular and/or cell surface protein kinases selected from EGFR, ErbB2, ErbB3, FGFR1, FGFR2, FGFR3, FGFR4, TrkA, NGFR, VEGFR (1, 2, 3), PDGFR ($\alpha$, $\beta$), TGF-$\beta$R (I, II, III), FLT3, Lck, Lyn, Src, c-Kit, c-Fms, Raf-1, B-Raf, RET, CSF-1R) in pterygium. In some cases the multikinase inhibitor has an IC50 against VEGFR (1, 2, 3) of <200 nM, an IC50 against PDGFR ($\alpha$, $\beta$) of <200 nM, and/or an IC50 against FGFR (1, 2, 3) of <1000 nM.

In some embodiments of all aspects, the multikinase inhibitor is selected from the group consisting of Afatinib, Amuvatinib, Axitinib, Cabozantinib, Canertinib, Cediranib, Ceritinib, Crenolanib, Crizotinib, Dabrafenib, Dacomitinib, Dasatinib, Erlotinib, Foretinib, Gefitinib, Golvatinib, Ibrutinib, Icotinib, Idelalisib, Imatinib, Lapatinib, Lenvatinib, Neratinib, Nilotinib, Nintedanib, Palbociclib, Pazopanib, Ponatinib, Quizartinib, Regorafenib, Ruxolitinib, Sorafenib, Sunitinib, Tandutinib, Tivantinib, Tivozanib, Trametinib, Vandetanib, Vatalanib, and Vemurafenib. In some cases, the antimetabolite is selected from the group consisting of Mitomycin C, 5-Fluorouracil, Floxuridine, Cytarabine, 6-azauracil, Azathioprine, Methotrexate, Mycophenolate Mofetil, and Thiotepa.

In some embodiments of all aspects, the multikinase inhibitor, the antimetabolite, or combination thereof is administered to the affected eye in the form of topical ocular formulation, an ointment, a gel, a sustained release semi-solid formulation, a sustained release solid formulation or ocular implant. In some cases, the multikinase inhibitor, the antimetabolite, or combination thereof is administered to the affected eye in the form topical ocular formulation and is administered topically to the affected eye.

In some instances, the topical ocular formulation is a solution, a suspension or an emulsion. In some cases, the topical ocular formulation also includes one or more pharmaceutically acceptable excipients selected from stabilizers, surfactants, polymer base carriers, gelling agents, organic co-solvents, pH active components, osmotic active components and with or without preservatives. In some cases, the sustained release semi-solid formulation, sustained release solid formulation or ocular implant is injected into the affected eye. In some embodiments, the sustained release semi-solid formulation, sustained release solid formulation or ocular implant further comprises a pharmaceutically acceptable excipient. In some cases, the sustained release semi-solid formulation, sustained release solid formulation or ocular implant includes a multikinase inhibitor, the antimetabolite, or combination thereof; and a biodegradable polymer selected from polylactic acid (PLA), polyglycolic acid (PLGA) and polylactic acid polyglycolic acid copolymers.

In some embodiments of all aspects, the administration is performed on pterygium patients.

In another aspect, the disclosure provides for a method for reducing hyperemia and symptoms thereof in in the pterygium, pinguecula and pseudopterygium of a patient in need of such treatment, including administering to an affected eye of the subject a therapeutically effective amount of a multikinase inhibitor.

In another aspect, the disclosure provides for a method for reducing or preventing pterygium recurrence in a subject in need of such treatment including administering to an affected eye of the subject a therapeutically effective amount of a multikinase inhibitor. In some embodiments of all aspects, the administration is performed prior to surgical removal of pterygium. In some instances, the administration is performed during a surgical procedure to removal of pterygium. In some cases, the administration is performed following surgical removal of pterygium.

In some embodiments of all aspects, the multikinase inhibitor has an IC50 against VEGFR (1, 2, 3) of <50 nM, an IC50 against PDGFR (α, β) of <100 nM, an IC50 against FGFR (1, 2, 3) of <150 nM, an IC50 against FGFR4 of <1000 nM, an IC50 against FLT3 of <50 nM, an IC50 against Lck of <50 nM, an IC50 against Lyn of <200 nM), and an IC50 against Src of <200 nM. In some cases, the multikinase inhibitor is selected from the group consisting of nintedanib {Methyl (3Z)-3-{[(4-{methyl[(4-methylpiperazin-1-yl)acetyl]amino}phenyl)amino] (phenyl)methylidene}-2-oxo-2,3-dihydro-1H-indole-6-carboxylate}, the free base, a hydrate, solvate or pharmaceutically acceptable salt of thereof. In some instances, the multikinase inhibitor is nintedanib free base or nintedanib esylate (ethanesulfonate salt).

In some embodiments of all aspects, the multikinase inhibitor is administered to the affected eye in the form of topical ocular formulation, a sustained release semi-solid formulation, a sustained release solid formulation or ocular implant. In some cases, nintedanib is administered to the affected eye in the form topical ocular formulation and is administered topically to the affected eye. In some cases, the topical ocular formulation is a solution, a suspension or an emulsion. In some embodiments of all aspects, the concentration of nintedanib in the topical ocular formulation is from 0.001% to 10% by weight of the total amount of the formulation.

In some embodiments of all aspects, the topical ocular formulation also includes one or more pharmaceutically acceptable excipients selected from stabilizers, surfactants, polymer base carriers, gelling agents, organic co-solvents, pH active components, osmotic active components and preservatives. In some cases, the sustained release semi-solid formulation, sustained release solid formulation or ocular implant is injected into the affected eye. In some instances, the sustained release semi-solid formulation, sustained release solid formulation or ocular implant includes nintedanib and a pharmaceutically acceptable excipient. In some cases, the amount of nintedanib in the sustained release semi-solid formulation, sustained release solid formulation or ocular implant is 1 μg to 100 mg. In some instances the sustained release semi-solid formulation, sustained release solid formulation or ocular implant comprises nintedanib; and a biodegradable polymers selected from polylactic acid (PLA), polyglycolic acid (PLGA) and a polylactic acid polyglycolic acid copolymer.

As used herein, the term "one or more" includes at least one, more suitably, one, two, three, four, five, ten, twenty, fifty, one-hundred, five-hundred, etc., of the item to which "one or more" refers.

The term "subject" refers to an animal or human, or to one or more cells derived from an animal or human. Preferably, the subject is a human. Subjects can also include non-human primates. A human subject can be known as a patient.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A provides results on day 12 and FIG. 1B provides results on day 14. The area of cornea neovascularization are shown for each treatment groups. Group 1: positive control sunitinib 0.05% TID; group 2: 0.2% nintedanib BID; group 3: 0.2% nintedanib TID; group 4: 0.05% nintedanib BID; group 5: 0.05% nintedanib TID; group 6: vehicle control TID. T-test significance levels comparing each group vs vehicle are shown by asterisk symbols.

Figure 2A:
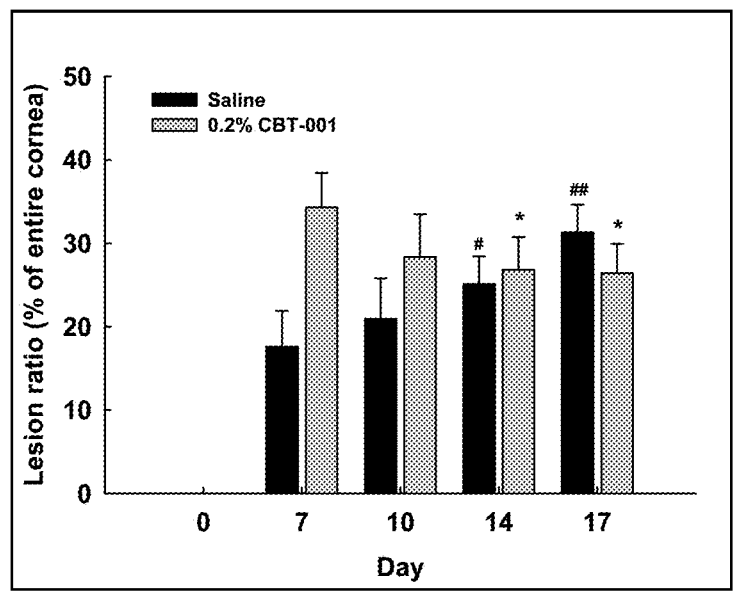
Figure 2B:
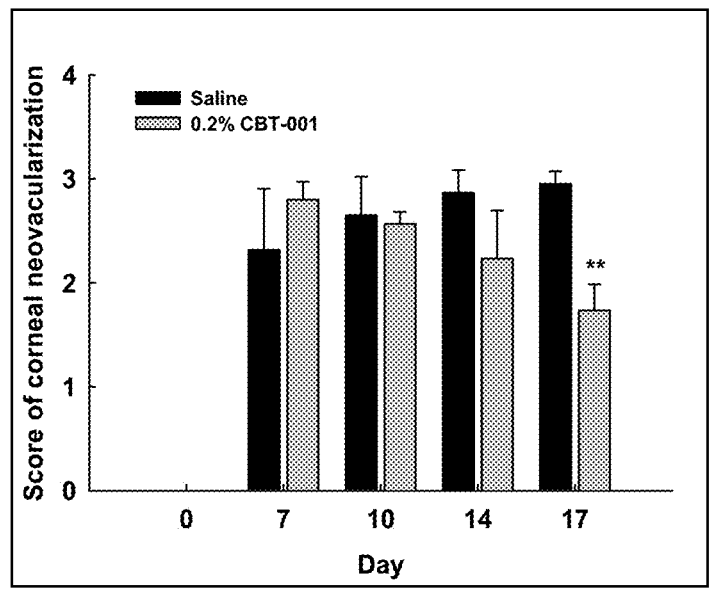

FIGS. 2A and 2B are graphs demonstrating the effects of nintedanib (CBT-001) in the human pterygium mouse model. (2A) 0.2% nintedanib reduced pterygium lesion area on mouse cornea. The pterygium lesion area on day 14 and day 17 are significantly smaller than the baseline level on day 7. In contrast, the pterygium area in the saline control eyes increased over the 10-day period with day 14 and 17 significantly more than day 7. (2B) 0.2% nintedanib reduced the neovascularization on cornea and the reduction was significant comparing levels on day 17 vs the baseline on day 7. In the saline control eye, the neovascularization slightly increased without statistically significant difference from baseline.

Figure 3A:
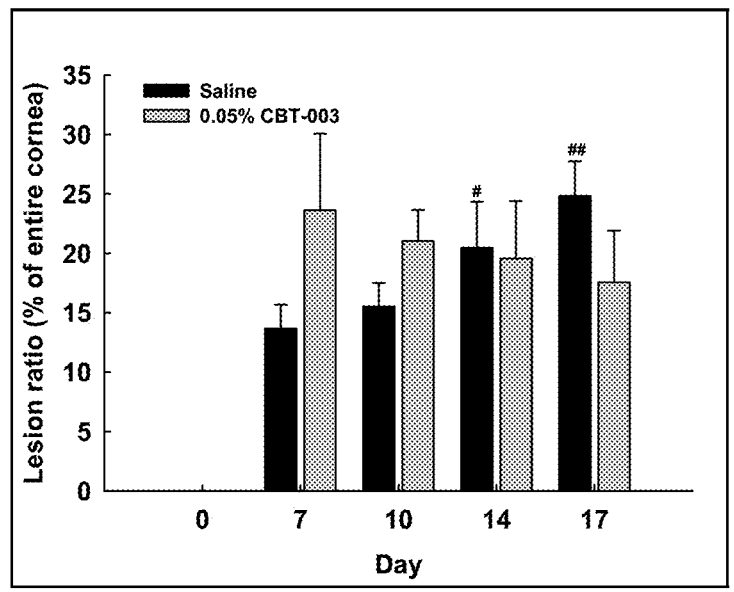
Figure 3B:
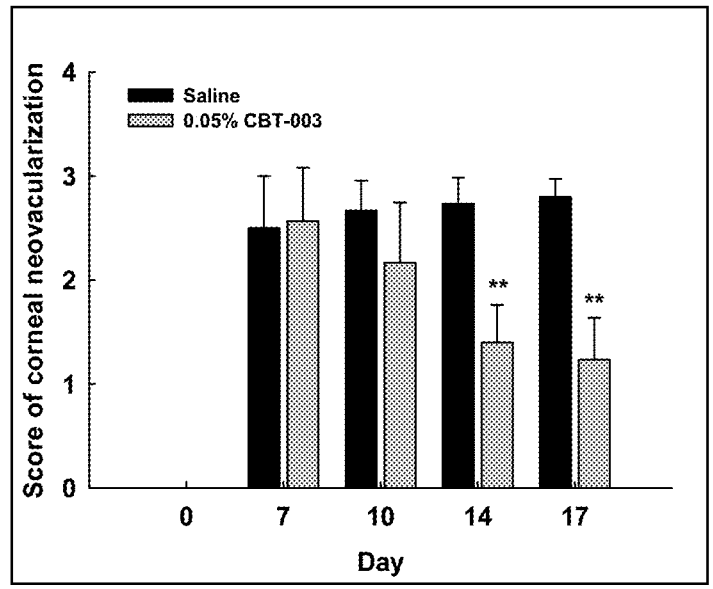

FIGS. 3A and 3B are graphs demonstrating the effects of sunitinib (CBT-003) in the pterygium mouse model. (3A) 0.05% sunitinib showed a trend of reduction of pterygium lesion area but the differences at each time points from the day 7 baseline are not statistically significant. The pterygium area in the saline control eyes increased over the 10-day period with day 14 and 17 significantly more than day 7. (3B) 0.05% sunitinib reduced the neovascularization on cornea and the reduction was significant comparing levels on day 14 and 17 vs the baseline on day 7. In the saline control eyes, the neovascularization did not change significantly.

Figure 4A:
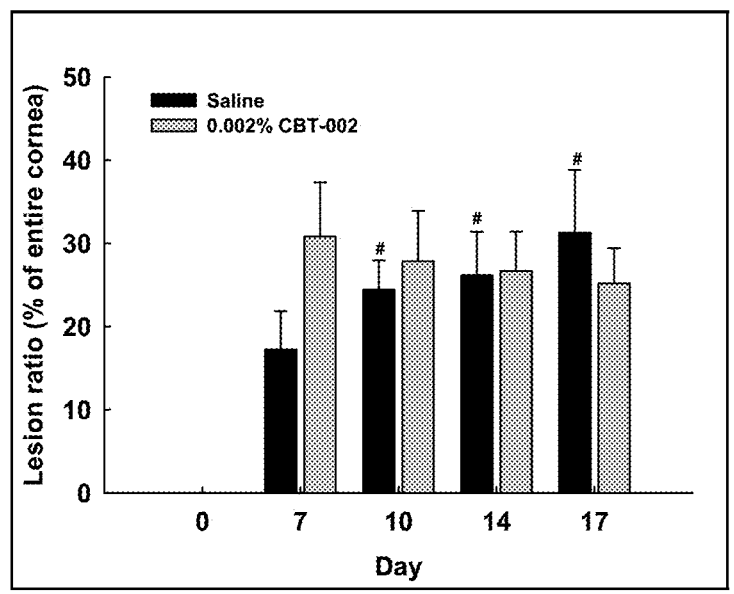
Figure 4B:
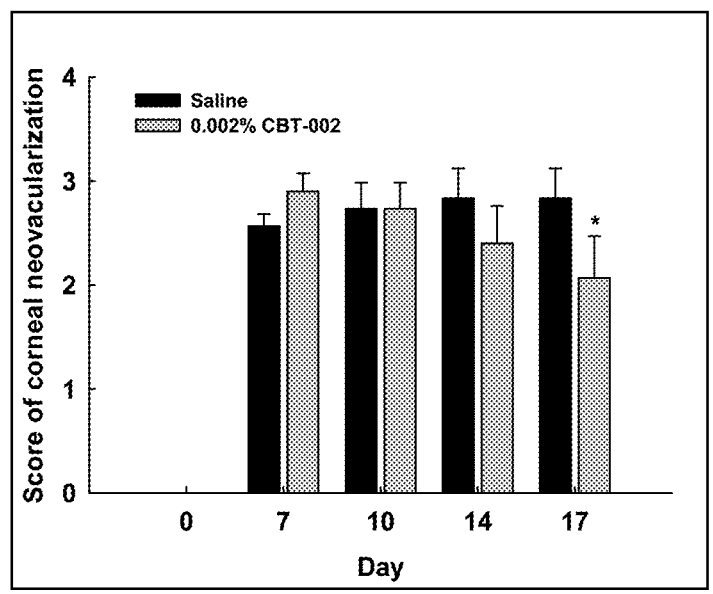

FIGS. 4A and 4B are graphs demonstrating the effects of mitomycin (CBT-002) in the pterygium mouse model. (4A) 0.002% mitomycin showed a trend of reduction of pterygium lesion area but the differences at each time points from the day 7 baseline are not statistically significant. The pterygium area in the saline control eyes increased with day 10, 14 and 17 significantly more than day 7. (4B) 0.002% mitomycin reduced the neovascularization on cornea and the reduction was significant comparing levels on day 17 vs the baseline on day 7. In the saline control eyes, the neovascularization did not change significantly.

Figure 5A:
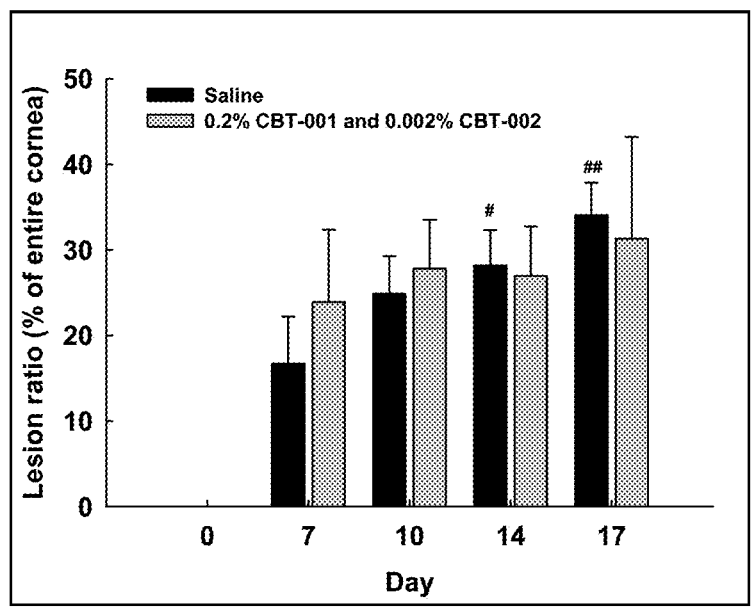
Figure 5B:
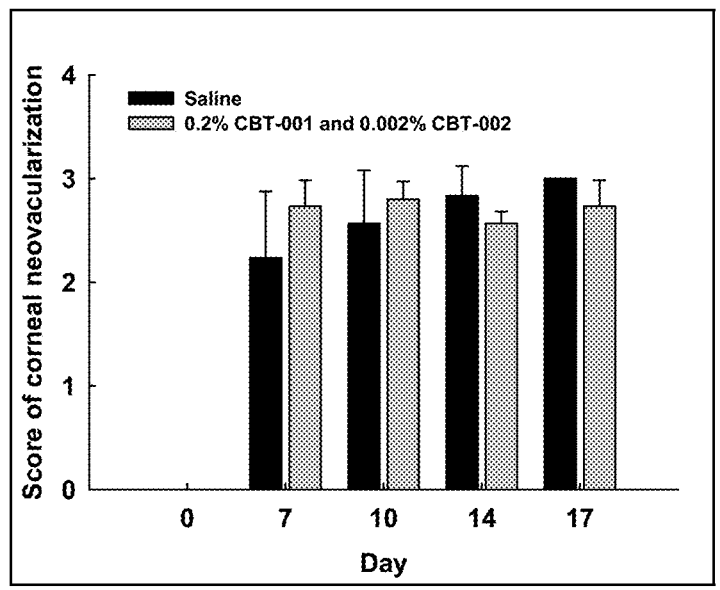

FIGS. 5A and 5B are graphs demonstrating the effects of combination of nintedanib (CBT-001) and mitomycin (CBT-002) in the pterygium mouse model. (5A) the pterygium area in the saline control eyes increased with day 14 and 17 significantly more than day 7 while the area didn't significantly increase in the combo treatment group. (5B) the neovascularization area did not change significantly in saline and combo treatment groups.

DETAILED DESCRIPTION

Pterygium is an ocular surface disease, where a fibrovascular growth extends from the nasal or temporal conjunctiva across the limbus onto the cornea. Pterygium patients often experience symptoms of ocular discomfort, hyperemia, and are at risk of visual impairment if the lesion encroaches on the visual axis. The incidence of pterygium is positively associated with lifetime sun exposure and other risk factors such as increasing age, male gender, and rural residency, whilst wearing glasses or a hat has been shown to have a protective effect. In addition, pterygia are more common in some occupational groups, such as welders, laborers, and those that work outdoors, which reflects a key role of ultraviolet (UV) exposure in the pathogenesis of this disease. Pterygia are often considered as benign tumors due to their invasive growth habit and propensity for recurrence, but not metastasis. The current understanding of the pathogenesis of pterygium is that multiple processes are involved and these may be divided into inherited factors, environmental triggers (UV light, viral infections), and factors that perpetuate its growth (cytokines, growth factors and matrix metalloproteinases). Among them, chronic UV exposure is the single most significant factor in the pathogenesis of pterygium. The relationship between UV exposure and pterygia is well supported by epidemiological studies and its association with other UV-related conditions such as photoaged skin, cataracts, climatic droplet keratopathy, and squamous cell and basal cell carcinomas. UV-activated molecular mechanisms, such as oxidative stress and growth factor receptor (GFR) signaling, lead to the synthesis and secretion of effector molecules such as cytokines, growth factors and matrix metalloproteinases that perpetuate the growth of the pterygia. UV is a well-known inducer of oxidative stress and a contributor to cutaneous photoaging. Oxidative stress, triggered by UV, mediates activation of epidermal growth factor receptors (EGFRs) and subsequent downstream signaling via the mitogen-activated protein kinase pathways.

Currently, there is no approved pharmacologic therapy to treat pterygia. Pterygium excision with conjunctival autograft transplantation remains the procedure of choice for definitive treatment of both primary and recurrent pterygia. While many of these lesions can be readily removed to the initial satisfaction of both surgeon and patient, the recurrence of pterygium could occur. Antimetabolites, such as 5-FU, and MMC have been used in conjunction with or after pterygium surgery to decrease the recurrence rate of pterygia (Almond et al., Pterygium: Techniques and Technologies for Surgical Success. Hovanesian J A. Ed. SLACK Incorporated. 2012; pp 55-63).

Pterygium is a multifactorial disease and several growth factors such as VEGF and PDGF are potential pathological factors. However, no drug against these growth factors has been developed to treat the disease. The anti-VEGF antibodies bevacizumab and ranibizumab have been tested in pterygium patients in the clinic around the world but the results are highly variable and it is not clear whether such treatment using antibodies are effective. A few studies reported that bevacizumab could stop pterygium growth but most of studies reported negative results. To date, there have been no reports of a small molecule anti-angiogenesis drug being tested in the clinic for pterygium. The human pterygium mouse model was developed recently with only two publications (Lee et al. Graefes Arch Clin Exp Ophthalmol. 2014; 252(4):609-18; Cox et al. Ophthalmology. 2010; 117(9): 1782-91). No anti-angiogenesis drugs have ever been tested in this model before. Provided below, for the first time, the inventors demonstrate that multikinase inhibitors with anti-angiogenesis activities effectively inhibit and/or stabilize pterygium growth and reduce pterygium tissue lesion size in the mouse model. In addition, the inventors demonstrate that antimetabolite provide analogous results. The present disclosure is based, in part, on these novel findings. Thus, the present disclosure provides compositions and methods of administering a multikinase inhibitor, an antimetabolite, or a combination of a multikinase inhibitor with an antimetabolite to treat pterygium by stabilizing the disease and inducing regression.

As used herein, the term "pterygium regression" means a decrease or reduction of the pterygium size in an affected eye. For example, the term "pterygium regression" means a decrease or reduction of the pterygium size in an affected eye by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

As used herein, the term "ocular hyperemia" or "hyperemia" refers to redness in an eye resulting from an excess of blood in the white of the eyes (sclera). The term "reducing hyperemia" means be reduction in redness and\or increase in whiteness in an affected eye. The reduction in redness and\or increase in whiteness can be confirmed or measured by methods well known to those skilled in the art, including visual assessment by a professional.

As used herein, the term "stabilizing pterygium" or "stabilization of the pterygium size" refers to means maintaining pterygium size in an affected eye.

As used herein, the term "pterygium recurrence" means the reappearance of pterygium in an eye following removal (e.g., surgical removal) of primary pterygium.

As used herein, the terms "therapeutically effective" and "effective amount" refer to that amount of an agent effective to produce the intended pharmacological, therapeutic or preventive result. The pharmacologically effective amount results in the amelioration of one or more symptoms of a disorder, or prevents the advancement of a disorder, or causes the regression of the disorder, or prevents the disorder. For example, with respect to inducing pterygium regression, a therapeutically effective amount refers to the amount of a therapeutic agent that reduces pterygium size, by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

Therapeutically effective dosages in the methods described herein can be determined by the treating physician. For example, the physician may begin treatment using manufacturer-recommended doses for the multikinase inhibitor or antimetabolite, and make adjustments based on the physician's observations of the effect of treatment. Further guidance is provided herein and in the Examples. In addition, clinical trials can be conducted to determine the doses that are effective to produce statistically significant treatment effects when a population of patients is treated.

The phrase "or combination thereof" or "in combination with" is intended to refer to all forms of administration that provide a first agent together with a second agent, such as a second inhibitory nucleic acid molecule or a chemotherapeutic agent, where the two are administered concurrently or sequentially in any order. For two or more agents to be administered in combination with each other, the agents need not be administered simultaneously or in the same formulation. Agents administered in combination with each other simultaneously present or have biological activity in the subject to which the agents are delivered. Determination of the presence of an agent in a subject can be readily determined by empirical monitoring or by calculations using known pharmacokinetic properties of the agents.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those with an increased likelihood of infection, those suspected of having cancer, those suspected of harboring an infection, etc.).

As used herein, the term "multikinase inhibitor" (MKI) refers to drug compounds (e.g., a small molecule) that reduce or inhibit the expression or activity of two or more kinases, including, for example, intracellular and/or cell surface protein kinases.

As used herein, "small molecule" is understood to refer to a chemical compound having a molecular weight below 2,000 daltons, more preferably between 200 and 1,000 daltons, and still more preferably between 300 and 700 daltons. It is preferred that these small molecules are organic molecules. In certain embodiments, "small molecule" does not include peptide or nucleic acid molecules.

Exemplary multikinase inhibitors for use in the methods described herein demonstrate certain kinase inhibition profiles. For example, multikinase inhibitors for use in the methods described herein can have a kinase inhibition profile with an IC50 against VEGFR (1, 2, 3) of $IC_{50} < 200$ nM, PDGFR ($\alpha$, $\beta$) of $IC_{50} < 200$ nM, and FGFR (1, 2, 3) of $IC_{50} < 1$ μM.

Exemplary multikinase inhibitors for use in the methods described herein include, for example, Afatinib, Amuvatinib, Axitinib, Cabozantinib, Canertinib, Cediranib, Ceritinib, Crenolanib, Crizotinib, Dabrafenib, Dacomitinib, Dasatinib, Erlotinib, Foretinib, Gefitinib, Golvatinib, Ibrutinib, Icotinib, Idelalisib, Imatinib, Lapatinib, Lenvatinib, Neratinib, Nilotinib, Nintedanib, Palbociclib, Pazopanib, Ponatinib, Quizartinib, Regorafenib, Ruxolitinib, Sorafenib, Sunitinib, Tandutinib, Tivantinib, Tivozanib, Trametinib, Vandetanib, Vatalanib, and Vemurafenib.

Nintedanib {Methyl (3Z)-3-{[(4-{methyl[(4-methylpiperazin-1-yl)acetyl]amino}phenyl)amino] (phenyl)methylidene}-2-oxo-2,3-dihydro-1H-indole-6-carboxylate} is an example of a multikinase inhibitor as described herein. Nintedanib inhibits primarily receptor tyrosine kinases including, for example vascular endothelial growth factor receptor (VEGFR 1-3), platelet-derived growth factor receptor (PDGFR $\alpha$ and $\beta$), fibroblast growth factor receptor (FGFR 1-4) and others (see Table 1 below) and displays unique kinase inhibition profile.

TABLE 1

| Kinase targets | $IC_{50}$(nM) | | | | | |
| --- | --- | --- | --- | --- | --- | --- |
| | Nintedanib | Sunitinib | Vandetanib | Sorafenib | Pazopanib | Vatalanib |
| VEGFR1 | 34 | 21 | | 9 | 7 | 77 |
| VEGFR2 | 21 | 34 | 40 | 28 | 15 | 37 |
| VEGFR3 | 13 | 3 | | 7 | 2 | 660 |

TABLE 1-continued

|         | Nintedanib | Sunitinib | Sorafenib | Pazopanib | Vandetanib |
|---------|-----------|-----------|-----------|-----------|------------|
| PDGFRα  | 59        | 143       | 933       | 73        |            |
| PDGFRβ  | 65        | 75        | 1129      | 215       | 580        |
| FGFR1   | 69        | 437       |           | 64        | 80         |
| FGFR2   | 37        | 852       |           |           | 350        |
| FGFR3   | 108       | 314       |           |           | 138        |
| FGFR4   | 610       |           |           |           |            |
| FLT3    | 26        | 4         |           | 45        | 619        |
| LCK     | 16        | 95        |           |           | 379        |
| Lyn     | 195       |           |           |           |            |
| Src     | 156       |           |           |           |            |
| c-Kit   |           | 40        | 1862      | 48        | 730        |
| c-Fms   |           | 5         |           | 6         |            |
| Raf-1   |           |           | 6         |           |            |
| B-Raf   |           |           | 22        |           |            |
| RET     |           | 232       | ?         |           |            |
| CSF-1R  |           |           |           |           |            |
| EGFR    |           |           | ?         |           |            |

|         | Axitinib | Cediranib | Regorafenib | Tivozanib | Motesanib | Linifanib |
|---------|----------|-----------|-------------|-----------|-----------|-----------|
| VEGFR1  | 0.1      | 5         | 13          | 30        | 2         | 3         |
| VEGFR2  | 0.2      | 0.5       | 4.2         | 6.5       | 3         | 4         |
| VEGFR3  | 0.2      | 3         | 46          | 15        | 6         | 190       |
| PDGFRα  | 5        | 36        |             | 40        | 84        |           |
| PDGFRβ  | 1.6      | 5         | 22          | 49        |           | 66        |
| FGFR1   |          | 26        | 202         | 530       |           |           |
| FGFR2   |          |           |             |           |           |           |
| FGFR3   |          |           |             |           |           |           |
| FGFR4   |          |           |             |           |           |           |
| FLT3    |          |           |             |           |           | 4         |
| LCK     |          |           |             |           |           |           |
| Lyn     |          |           |             |           |           |           |
| Src     |          | 130       |             | 960       |           |           |
| c-Kit   | 1.7      |           | 7           | 78        | 8         | 14        |
| c-Fms   |          |           |             |           |           |           |
| Raf-1   |          |           | 2.5         |           |           |           |
| B-Raf   |          |           | 19          |           |           |           |
| RET     |          |           |             |           | 59        |           |
| CSF-1R  | 73       | 110       |             |           |           | 3         |
| EGFR    |          |           |             |           |           |           |

Nintedanib data from Hilberg et al, Cancer Res 2008; 68: (12), 4774-4782. Sunitinib, sorafenib and pazopanib data from British Journal of Cancer 2009; 101, 1717-1723. Other data from selleckchem database. For sunitinib, some additional targets are not listed.

As used herein, the term 'antimetabolite" refers to drug compounds that inhibit the use of a metabolite and thus reduce, prevent or inhibit the growth of rapidly dividing cells. For example, antimetabolites of the present disclosure may inhibit DNA duplication via different mechanisms resulting in the reduction, prevention or inhibition of cell division. Exemplary antimetabolites for use in the methods described herein include, for example, purine and pyramiding analogs such as 5-Fluorouracil (5-FU), antibiotics such as Mitomycin-C (MMC), and anti-folate compounds such as Methotrexate. Exemplary antimetabolites for use in the methods described herein include, for example, Mitomycin C, 5-Fluorouracil, Floxuridine, Cytarabine, 6-Azauracil, Azathioprine, Methotrexate, Mycophenolate Mofetil, and Thiotepa.

Mitomycin-C (MMC) is an example of an antimetabolie as described herein. MMC is an antibiotic and antineoplastic agent, which undergoes reductive activation to become a potent alkylating agent. Under hypoxic conditions, it interferes with DNA replication by cross-linking DNA, usually at the N2 position of guanine; as such it is most effective in cells that are actively dividing. Under aerobic conditions, it generates toxic oxygen radicals capable of nonspecific interference with RNA and protein synthesis. It has been used intravenously as an antineoplastic agent against tumors of the gastrointestinal tract, pancreas, lung, and breast, among others. It has also been used in an intravascular application for bladder cancer.

5-FU is an example of an antimetabolite as described herein. 5-FU is a fluorinated pyrimidine and its primary antimetabolic effect is believed to be the inhibition of thymidylate synthetase, which leads to a lack of intracellular thymidine for DNA production. Additional effects of 5-FU are attributed to inhibition of other enzymes or the incorporation of its metabolites into RNA.

Multikinase inhibitors and antimetabolites are well known to those having ordinary skill in the art and are commonly used for treating cancers.

The compositions and methods described herein are useful for treating patients at an early stage of pterygium or pinguecula or pseudopterygium, where patients experience ocular discomfort, hyperemia, irritation, blurred vision, foreign body sensation and pain, the treatment goal is to reduce hyperemia and symptoms. For example, the disclosure provides compositions and methods of treatment using nintedanib, a multikinase inhibitor, in a suitable ocular dosage form to reduce hyperemia and other symptoms.

The compositions and methods described herein are also useful for treating patients at the late stage of pterygium, where the fibrovascular growth extends from conjunctiva across limbus to central cornea to encroach the visual axis, bare sclera pterygium excision with conjunctival autograft transplantation or with amniotic membrane transplantation would be the procedure of choice for treatment. Although the risk of recurrence with the advancement of surgical techniques and adjunctive therapies has decreased significantly, recurrences continue to be a significant problem for surgeons and patients. To prevent pterygium recurrence, the disclosure provides compositions and methods of treatment using nintedanib in a suitable ocular dosage form to reduce pterygium recurrence.

The compositions and methods described herein are also useful for treating hyperemia and reducing symptoms associated therewith, as shown in the rabbit suture model study provided in Example 1. In this example, nintedanib had excellent efficacy in inhibiting suture-induced neovascularization in cornea. Table 2 below shows that the percent change of neovascular area is substantially reduced in the eyes treated with nintedanib comparing to the vehicle group. The efficacy of nintedanib is dependent on dose concentration and dose frequency regimen. Interestingly, nintedanib showed a clear trend of superiority to sunitinib in reducing neovascular area. While the two kinase inhibitors have substantial target overlaps, distinct efficacies were noted in this rabbit model. Another advantage of nintedanib is that it inhibits a smaller number of targets than sunitinib, allowing for better safety margins and higher doses. In fact, as shown in Example 1, a potential toxicity of abnormal lens with incomplete lenticular opacity was observed in one rabbit during the dosing period for sunitinib group while none was observed for nintedanib groups. In addition, in an in vivo corneal suture rabbit model study where rabbits were placed sutures in the cornea and dosed with sunitinib for 7 days, an anterior chamber cellular reaction was observed on day 1 (Perez-Santonja J J et al, Am J Ophthalmol. 2010; 150(4): 519-528). Iris surface yellowish staining, which represents sunitinib deposits on the iris surface was observed during the whole dosing period. Sunitinib settles on the inferior quadrant of the iris, starting at the pupil rim and spreads to some extent between the pupil and the anterior chamber angle, which could potentially lead to toxic effects in a long term. Furthermore, significant toxicity of sunitinib was seen at concentration of >3.3 μg/mL after 24 hours of incubation with human corneal epithelial cell (Bayyoud T et al., Current Eye Research, 39(2): 149-154, 2014).

Nintedanib and sunitinib both inhibit the key VEGFR and PDGFR families with a few non-overlapping targets (see Table 1). But the unique set of kinase targets of nintedanib seems to make it more effective and safe than sunitinib, indicating that nintedanib may be one of the most powerful multikinase inhibitors for reducing corneal neovascularization. The unique profile for the inhibition of the following intracellular and/or cell surface protein kinases at the maximum in vitro IC50 are specified as VEGFR (1, 2, 3) (IC50<50 nM), PDGFR ($\alpha$, $\beta$) (IC50<100 nM), FGFR (1, 2, 3) (IC50<150 nM), FGFR4 (IC50<1000 nM), FLT3 (IC50<50 nM), Lck (IC50<50 nM), Lyn (IC50<200 nM), and Src (IC50<200 nM). Three targets of FGFR4, Lyn and Src, are not inhibited by sunitinib or other common kinases inhibitors and these may differentiate nintedanib from sunitinib and others. In addition, the nintedanib's potencies on FGFR1-3 are substantially higher than that of sunitinib that may also contribute to the superior efficacy of nintedanib in the cornea suture rabbit model.

The compositions and methods described herein are also useful for treating patients at a mid-stage of pterygium, where fibrovascular growth extends from conjunctiva to limbus and cornea. At the mid stage of pterygium, the goal is to stabilize pterygium progression to delay or to avoid surgery for removing pterygium or even to induce pterygium regression from visual axis/central cornea. To achieve this goal, the disclosure provides compositions and methods of treatment using a multikinase inhibitor, an antimetabolite, or a combination of both in a suitable ocular dosage form.

An example of the compositions and methods for the treatment of an affected eye using a multikinase inhibitor to stabilize pterygium and to induce regression of pterygium are provided in Example 2 below, where the effect of such compositions on human pterygium cell growth on the cornea of immune deficient mice are shown. In this study, nintedanib and sunitinib prevented the growth of human pterygium on mouse cornea and nintedanib significantly reduced the size of pterygium. As shown in Table 3, provided below, the pterygium cells grew throughout the treatment period up to day 17, while in the groups treated with nintedanib, sunitinib, MMC or the combination of nintedanib and MMC, pterygium cells either didn't grow or regressed in the case of nintedanib. Accordingly, the inventors' novel insights from the mouse model indicated that it is possible to use a multikinase inhibitor, such as nintedanib or sunitinib, to stop pterygium growth or even to induce regression of pterygium tissue. As an example, the target kinase profiles of a multikinase inhibitors for used in the compositions and methods described herein can target the following kinases at

TABLE 2

| | Neovascular Area Mean Percent Change over Day 7 Baseline (− sign indicates decrease) | | | | | |
|---|---|---|---|---|---|---|
| | 0.05% sunitinib TID | 0.2% nintedanib BID | 0.2% nintedanib TID | 0.05% nintedanib BID | 0.05% nintedanib TID | Vehicle TID |
| Day 10 (after 2 days of treatment) | 10.80 | 12.09 | −16.84 | 64.08 | 1.99 | 199.68 |
| P value vs sunitinib | | 0.96 | 0.247 | 0.090 | 0.783 | 0.003 |
| Day 12 (after 4 days of treatment) | 49.72 | 37.15 | −13.80 | 45.56 | −27.87 | 189.01 |
| P value vs sunitinib | | 0.67 | 0.074 | 0.917 | 0.016 | 0.079 |
| Day 14 (after 6 days of treatment) | 98.38 | 73.51 | −1.51 | 99.48 | 32.66 | 349.43 |
| P value vs sunitinib | | 0.54 | 0.009 | 0.984 | 0.093 | 0.057 | the specified in vitro $IC_{50}$: VEGFR (1, 2, 3) ($IC_{50}$<200 nM), PDGFR (α, β) ($IC_{50}$<200 nM), FGFR (1, 2, 3) ($IC_{50}$<1 μM).

TABLE 3

Pterygium Lesion as Percentage of Cornea area (Day 7 is baseline)

| % Change | Day 7 | | Day 10 | | Day 14 | | Day 17 | |
|---|---|---|---|---|---|---|---|---|
| | Saline | Drug | Saline | Drug | Saline | Drug | Saline | Drug |
| Vehicle | 15.4 | 16.2 | 20.9 | 18.3 | 23.6 | 24.3 | 28.3 | 25.4 |
| 0.2% nintedanib | 17.2 | 34.0 | 20.1 | 27.3 | 25.9* | 26.5* | 30.1** | 25.9* |
| 0.002% MMC | 17.0 | 30.9 | 24.8* | 27.5 | 26.1* | 26.8 | 29.9* | 24.0 |
| 0.05% sunitinib | 13.7 | 23.3 | 15.9 | 21.3 | 20.6* | 19.1 | 24.8* | 17.6 |
| 0.2% nintedanib + 0.002% MMC | 16.8 | 22.0 | 23.9 | 27.8 | 28.5* | 26.4 | 32.5* | 30.6 |

TTEST vs day 7: P < 0.05,*; P < 0.01,; P < 0.001, *

The compositions and methods described herein are also useful for treating patients using an antimetabolite inhibitor of epithelial cell and fibroblast proliferation to stabilize pterygium and to induce regression of pterygium (see Example 2). As shown in Table 3 above, mitomycin C (MMC) was able to prevent the growth of human pterygia cells and showed a trend of reducing the size of the pterygia tissue on cornea.

Given the multifactorial nature of pterygium, treatments by a combination of drugs may be necessary to achieve the optimal effects. As shown in Table 3, the pterygium cells on cornea treated with the combination of nintedanib and MMC didn't show significant growth while the saline control grew significantly.

Formulations and Dosing Regimen

The methods described herein include the manufacture and use of pharmaceutical compositions, which include compounds identified by a method described herein as active ingredients. Also included are the pharmaceutical compositions themselves.

Pharmaceutical compositions typically include pharmaceutically acceptable excipients. As used herein the language "pharmaceutically acceptable excipient" or "pharmaceutically acceptable carrier" includes saline, solvents, dispersion media, coatings, antibacterial and antifungal agents, isotonic and absorption delaying agents, and the like, compatible with pharmaceutical administration.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions, suspensions or emulsions used for ophthalmic application can include the following components: a sterile diluent such as water for injection, saline solution, fixed oils, polyethylene glycols, glycerin, propylene glycol or other synthetic solvents; antibacterial agents; antioxidants; chelating agents; buffers such as acetates, citrates or phosphates and agents for the adjustment of tonicity such as sodium chloride or dextrose. pH can be adjusted with acids or bases, such as hydrochloric acid or sodium hydroxide.

Pharmaceutical compositions suitable for injectable use can include sterile aqueous solutions (where water soluble) or dispersions and sterile powders for the extemporaneous preparation of sterile injectable solutions or dispersion. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially.

The pharmaceutical compositions can be included in a container, pack, or dispenser together with instructions for administration.

Compositions and formulations including a multikinase inhibitor, an antimetabolite, or a multikinase inhibitor in combination with an antimetabolite, as described herein, can be administered topically or as an injection of semi-solid formulation or solid implant, or by any other suitable methods known in the art. While it is possible to use an agent disclosed herein for therapy as is, it may be preferable to administer the agent as a pharmaceutical formulation, e.g., in admixture with a suitable pharmaceutical excipient, diluent, or carrier selected with regard to the intended route of administration and standard pharmaceutical practice.

Pharmaceutical formulations include at least one active compound, in association with a pharmaceutically acceptable excipient, diluent, and/or carrier.

Administration of a composition or formulation can be once a day, twice a day, three times a day, four times a day or more often. Frequency may be decreased during a treatment maintenance phase of the treatment, e.g., once every second or third day instead of every day or twice a day. The dose and the administration frequency can be adjusted based on the judgment of the treating physician, for example taking into account the clinical signs, pathological signs and clinical and subclinical symptoms of a disease of the conditions treated with the present methods, as well as the patient's clinical history.

It will be appreciated that the amount of an agent disclosed herein required for use in treatment will vary with the route of administration, the nature of the condition for which treatment is required, and the age, body weight and condition of the patient, and will be ultimately at the discretion of the attendant physician. Compositions will typically contain an effective amount of the active agent(s), alone or in combination. Preliminary doses can be determined according to animal tests, and the scaling of dosages for human administration can be performed according to art-accepted practices.

Length of treatment, i.e., number of days, will be readily determined by a physician treating the subject; however, the number of days of treatment may range from about 1 day to about 365 days. As provided by the present methods, the efficacy of treatment can be monitored during the course of treatment to determine whether the treatment has been successful, or whether additional (or modified) treatment is necessary.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). Dosage s dosage forms for the multikinase inhibitor, the antimetabolite and their individual dose strength in the combination therapy can be readily determined by the ordinarily skilled artisan, and can e.g., be obtained in animal models and in clinical studies reported in the literatures, for determining dosage, safety and efficacy according to standard methods known in the art. The exact formulation, route of administration and dosage can be chosen by the individual physician in view of the patient's condition.

Dosage strengths of the multikinase inhibitor include, for example, about 0.001 to about 100.0 mg, about 0.01 to about 90 mg, about 0.1 mg to about 75 mg, about 0.25 to about 50 mg, about 0.5 to about 25 mg, about 0.75 to about 20 mg, about 1.0 to about 15 mg, about 1.25 to about 10 mg, about 1.5 to about 5.0 mg, about 1.75 to about 2.5 mg, e.g., 0.001 mg, 0.01 mg, 0.1 mg, 0.25 mg, 0.5 mg, 0.75 mg, 1.0 mg, 1.25 mg, 1.5 mg, 1.75 mg, 2.0 mg, 2.5 mg, 5.0 mg 10.0 mg 15.0, mg 25.0 mg, 30.0 mg, 40.0 mg, 50.0 mg, 60.0 mg, 75.0 mg, or 100.0 mg of the multikinase inhibitor. For example, dosage strengths of nintedanib include, for example, 0.1 mg, 0.25 mg, 0.5 mg, 0.75 mg, 1.0 mg, 1.25 mg, 1.5 mg, 1.75 mg, 2.0 mg, 2.5 mg, 5.0 mg 10.0 mg 15.0, mg 25.0 mg, 30.0 mg, 40.0 mg, 50.0 mg, 60.0 mg, 75.0 mg, or 100.0 mg of nintedanib.

Compositions for use in the present methods may include a multikinase inhibitor at a concentration of 0.001% to 10% by weight or by volume the total amount of composition. For example, an aqueous composition comprises 0.001%, 0.01%, 0.1%, 0.5%, 1.0%, 1.5%, 2.0%, 5.0% or up to 10% nintedanib.

Dosage strengths of the antimetabolite include, for example, about 0.001 to about 100.0 mg, about 0.01 to about 90 mg, about 0.1 mg to about 75 mg, about 0.25 to about 50.0 mg, about 0.5 to about 25 mg, about 0.75 to about 20 mg, about 1.0 to about 15 mg, about 1.25 to about 10 mg, about 1.5 to about 5.0 mg, about 1.75 to about 2.5 mg, e.g., 0.001 mg, 0.01 mg, 0.1 mg, 0.25 mg, 0.5 mg, 0.75 mg, 1.0 mg, 1.25 mg, 1.5 mg, 1.75 mg, 2.0 mg, 2.5 mg, 5.0 mg 10.0 mg 15.0, mg 25.0 mg, 30.0 mg, 40.0 mg, 50.0 mg, 60.0 mg, 75.0 mg, or 100.0 mg of the antimetabolite. For example, dosage strengths of MMC include, for example. 0.1 mg, 0.25 mg, 0.5 mg, 0.75 mg, 1.0 mg, 1.25 mg, 1.5 mg, 1.75 mg, 2.0 mg, 2.5 mg, 5.0 mg 10.0 mg 15.0, mg 25.0 mg, 30.0 mg, 40.0 mg, 50.0 mg, 60.0 mg, 75.0 mg, or 100.0 mg of MMC.

Compositions for use in the present methods may include an antimetabolite at a concentration of 0.001% to 10% by weight or by volume the total amount of composition. For example, an aqueous composition comprises 0.001%, 0.01%, 0.1%, 0.5%, 1.0%, 1.5%, 2.0%, 5.0% or up to 10% MMC.

As will be familiar to those skilled in the art, administration to the eye of an aqueous solution may be in the form of "drop" or number of drops (e.g. of a multikinase inhibitor solution, an antimetabolite solution or combination thereof) from a dropper or pipette or other dedicated sterile device. Such drops will typically be up to 50 microliters in volume, but maybe smaller e.g. less than 10 microliters.

EXAMPLES

The invention is further described in the following examples, which do not limit the scope of the invention described in the claims.

Example 1: Rabbit Cornea Suture Model of Neovascularization and Hyperemia

The rabbit cornea suture model was established to assess drug effects on cornea neovascularization (Ko et al. Cornea. 2013; 32(5): 689-695; Perez-Santonja et al. Am J Ophthalmol. 2010; 150(4):519-528). Nintedanib was studied in this model for its anti-neovascularization activity.

Topical Ocular Formulations

Topical compositions comprising 0.2% or 0.05% nintedanib in 10% 2-hydroxypropyl beta cyclodextrin in phosphate buffer solution, pH 7.4 were prepared. In addition, a composition comprising 0.05% sunitinib was prepared in the same vehicle to serve as positive control.

Animals and Treatment Procedure

Thirty six female Zealand White rabbits were used to perform the study. Briefly, five sutures were placed in the upper cornea of the right eye of each animal on Day 1 to induce neovascularization. The animals were treated in both eyes as described in Table 4.

TABLE 4

| Dosing Period | Group | Treatment | Dosing Frequency | Number of Females |
|---|---|---|---|---|
| Days 1 to 7 | 1 | Saline | Once daily | 6 females |
|  | 2 | Saline | Once daily | 6 females |
|  | 3 | Saline | Once daily | 6 females |
|  | 4 | Saline | Once daily | 6 females |
|  | 5 | Saline | Once daily | 6 females |
|  | 6 | Saline | Once daily | 6 females |

TABLE 4-continued

| Dosing Period | Group | Treatment | Dosing Frequency | Number of Females |
|---|---|---|---|---|
| Days 8 to 15 | 1 | 0.05% sunitinib solution | TID | 6 females |
| | 2 | 0.2% nintedanib solution | BID | 6 females |
| | 3 | 0.2% nintedanib solution | TID | 6 females |
| | 4 | 0.05% nintedanib solution | BID | 6 females |
| | 5 | 0.05% nintedanib solution | TID | 6 females |
| | 6 | Saline (OD), Vehicle (OS) | TID | 6 females |

BID: Twice per day (approximately 10 to 12 hours apart).
TID: Three times per day (approximately 6 to 8 hours apart).
OD = right eye.
OS = left eye.
Both eyes were dosed, the dose volume was approximately 40 μL/eye.
Note:
The first dose of saline on Day 1 was done 4 hours post suture placement.

During the study, the animals were closely observed for various ocular indications as well as general physical conditions including body weight. Ocular images were taken on days 7, 10, 12, 14, 21, 28 for analysis.

Data Analysis

NIH ImageJ® software was used to analyze the ocular images. Each image was opened in ImageJ®, the scale was calibrated using the ruler in the photograph and the neovascularized area on the cornea near the suture was selected by the selection tool. The area in mm$^2$ was calculated by measurement tool in the software, recorded in excel and the image was captured and saved. Two-tailed t-TEST was used to determine whether pairs of groups are significantly different. The results were plotted as histograms of average with standard deviation for easy comparison.

Results and Discussions

Figure 1A:
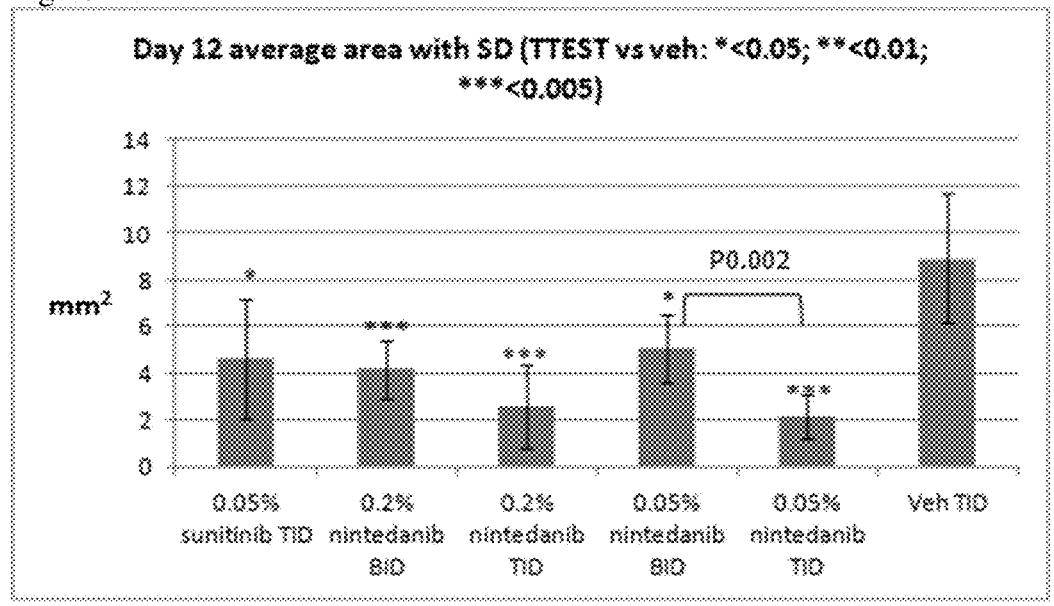
FIGS. 1A and 1B are graphs demonstrating the anti-vascularization efficacies of nintedanib in a rabbit cornea suture model.
Figure 1B:
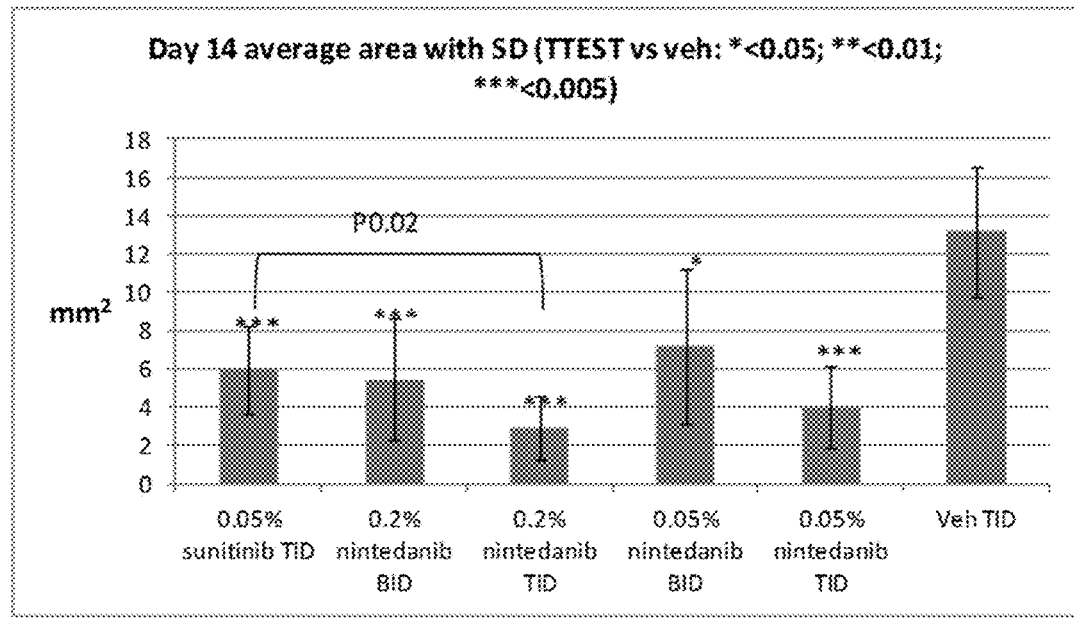

The results of this study are summarized below in FIGS. 1A and 1B and Table 5. The results demonstrate that nintedanib had a marked inhibitory effect on suture-induced neovascularization in the rabbit cornea. Higher dose of 0.2% nintedanib showed improved efficacy compared with 0.05% nintedanib, while more frequent dosing regimen of TID dosing showed improved efficacy compared with BID dosing. Surprisingly, nintedanib showed a clear trend of superiority to the positive control sunitinib in reducing neovascular area in this model.

In the rabbit suture model, sunitinib has previously been shown to inhibit vascularization more effectively than bevacizumab, an anti-VEGF antibody (Ko et al. Cornea. 2013; 32(5): 689-695; Pérez-Santonja et al. Am J Ophthalmol. 2010; 150(4):519-528). Their observation suggested that small molecule kinase inhibitors targeting multiple receptor-tyrosine-kinase pathways may have advantages over antibody drugs targeting a very selective pathway. The present results showed that nintedanib also inhibited neovascularization very effectively in the suture model. Quite unexpectedly, the inventors found that kinase inhibitors with substantial kinase target overlaps can still have different efficacies. Although nintedanib and sunitinib both inhibit the key VEGFR family, they have several non-overlapping targets. As shown in Table 1, the target profile of nintedanib is different from that of sunitinib as well as several other MKI's considered very similar in the research community. The special set of kinase targets of nintedanib seems offer at least two surprising advantages: 1) it makes nintedanib a highly effective inhibitor of neovascularization, more so than sunitinib, as demonstrated in the rabbit suture model; 2) it targets fewer kinases than sunitinib, allowing for better safety margins and higher doses. Accordingly, it is understood that nintedanib has demonstrated an improved efficacy and a better safety profile as compared with sunitinib.

TABLE 5

| Neovascular Area in mm$^2$ with TTEST P Value Against Sunitinib control | | | | | | |
|---|---|---|---|---|---|---|
| | 0.05% sunitinib TID | 0.2% nintedanib BID | 0.2% nintedanib TID | 0.05% nintedanib BID | 0.05% nintedanib TID | Veh TID |
| Day 10 (after 2 days of treatment) | 3.58 | 3.32 | 2.48 | 5.97 | 3.23 | 10.09 |
| P value vs sunitinib | | 0.819 | 0.283 | 0.04 | 0.780 | 0.004 |
| Day 12 (after 4 days of treatment) | 4.62 | 4.15 | 2.56 | 5.03 | 2.14 | 8.91 |
| P value vs sunitinib | | 0.697 | 0.153 | 0.749 | 0.055 | 0.03 |
| Day 14 (after 6 days of treatment) | 5.96 | 5.44 | 2.88 | 7.20 | 4.01 | 13.16 |
| P value vs sunitinib | | 0.750 | 0.024 | 0.532 | 0.159 | 0.002 |

The rationale of our claim is supported by previous findings in cancer research, a field where MKIs are used extensively. For cancer, some MKIs with substantial overlapping targets could still have very different efficacy in patients. For example, many small-molecule MKIs with overlapping targets were tested in non-small-cell-lung-cancer (NSCLC) patients, but interestingly, only nintedanib showed efficacy and is approved for combination therapy with other drugs (Hall R D et al. Transl Lung Cancer Res. 2015; 4(5), 515-23). Observations like this indicated that the target profile of a kinase inhibitor can dramatically affect efficacy in certain indications.

Our novel insights are summarized as following: First, in general, small molecule MKIs with certain target profiles are better than antibody drugs for treating abnormal cornea neovascularization. Although this was hinted by previous studies, it was based on a single pair of comparison between bevacizumab and sunitinib. Now, our study of nintedanib added much more weight to this theory. Second, our novel idea is that each MKI has its unique target profile and not all MKIs will be equally safe and efficacious in treating pterygium symptoms. Without being bound by theory, we believe nintedanib offers a unique profile that will provide one of the most effective and safe treatments for pterygium.

In summary, the unique target profile of nintedanib can make it a more effective and safer drug for treating pterygium. Nintedanib inhibits FGFR1-3 more effectively than sunitinib. It also inhibits FGFR4, Lyn, Src that are not targets of sunitinib (see Table 1 in the background section). In addition, nintedanib is expected to have better safety profiles than sunitinib because sunitinib is known to hit more kinases than compounds in the same class (Kumar et al. Br J Cancer. 2009; 101(10):1717-23) and it inhibits some additional kinases not listed Table 1. Some of these, such as the CaMK family, are important for normal cellular functions and their inhibition could have safety issues.

Example 2: The Human Pterygium Mouse Model

The human pterygium mouse model was described to assess human pterygium growth on the cornea of immune deficient mouse (Lee et al., Graefes Arch Clin Exp Ophthalmol. 2014; 252(4):609-18). The present study investigated the effects of several drugs' effect on pterygium growth. The drugs are nintedanib, sunitinib and mitomycin C.

Topical Ocular Formulations

The articles tested were prepared in 10% 2-hydroxypropyl beta cyclodextrin in phosphate buffer solution, pH 7.4. The detailed information of the formulation is disclosed in a section below.

Animals

Seven weeks old male athymic nude mice were adapted under pathogen-free conditions in enclosed filter-topped cages.

Human Pterygium Primary Cell Culture

Human pterygium epithelial cells (hPECs) were isolated and cultured from specimen collected after surgical excision. All participants provided written informed consent after having received a comprehensive explanation of the study. Fresh pterygium specimens were cultured on surfaces coated with collagen (rat tail collagen type I) for three days in DMEM/F12 medium supplemented with 10% bovine calf serum, 0.5% dimethyl sulfoxide, and 1% antibiotic/anti-mycotic, during which time the cells migrated from the explant. Then, the explant was removed, and the medium was changed to keratinocyte-serum free medium with 5% BCS, and 1% antibiotic/anti-mycotic to further promote epithelial cell growth.

Induction of Human Pterygium

Mice were anesthetized by i.p. injection of ketamine (30 mg/kg) and rumpun (2.5 mg/kg) for subconjunctival injection. Pterygium in mouse was induced by injecting $1 \times 10^4$ hPECs in the nasal subconjunctival space of both eyes on day 0. After 7 days, the mice induced with hPEC were subjected to test.

Treatments

Animals were treated as following:
Group 1: vehicle right eye and saline left eye;
Group 2: 0.2% nintedanib right eye and saline left eye;
Group 3: 0.002% mitomycin right eye and saline left eye;
Group 4: 0.05% sunitinib right eye and saline left eye;
Group 5: 0.2% nintedanib and 0.002% mitomycin mixture right eye and saline left eye.

Animals were treated by nasal subconjunctival injection on day 7, 10, and 14 and by topical eye drop dosing QID on day 8, 9, 11, 12, 13, 15, and 16. Before each injection and also on day 17, the eyes were observed and captured by using stereo microscope.

Clinical Observation

Mice were observed daily for clinical signs of toxicity during experiment. The eyes were observed and captured before injection and at day 17. All findings including illness, diagnoses, and therapy were recorded. The weights of mice were measured at day 0, 7, day 11, day 15 and day 17.

Corneal Pterygium Analysis

Image analysis of the photograph was performed using ImageJ® to measure the lesion size at day 0, 7, 10, 14 and 17. These data were calculated as the ratio of the pterygium to the entire cornea.

Corneal Neovascularization Analysis

The clinical features of the eyes of all mice were evaluated. The extent of corneal neovascularization (NV) was scored from 0 through 3, where 0=no NV, 1=NV confined to the corneal periphery, 2=NV extending up to the pupil margin, and 3=NV extending beyond the pupil margin into the central cornea.

Statistical Analysis

Data were analyzed by SPSS version 18.0 for Windows (SPSS, Chicago, Ill.) and are expressed as the mean±standard deviation.

Results and Discussions

The results are shown in FIGS. 2A-B, 3A-B, 4A-B and 5A-B, and also summarized in Table 4 above. In the human pterygium mouse model, 0.2% nintedanib treatment led to a reduction of the pterygium area on day 14 and day 17 in comparison to the baseline level on day 7 (FIGS. 2A and 2B). In contrast, the control saline treated eyes showed increases of pterygium areas on day 14 and day 17. Nintedanib also reduced neovascularization score on the cornea during the treatments with the level on day 17 showing a significant difference from the baseline on day 7 (FIGS. 2A and 2B) while the control eyes showed a small non-statistically significant increase of neovascularization (FIGS. 2A and 2B). In this model, 0.002% mitomycin and 0.05% sunitinib also showed a trend of reduction in pterygium areas but didn't reach statistical significance at any of the time points (FIGS. 3A-3B, 4A-4B). In contrast, the control saline treated eyes showed increases of pterygium areas on nearly all the time points and increases are nearly linear over time. Mitomycin and sunitinib also reduced neovascularization score, with significant reductions on day 17 for mitomycin and on day 14 and day 17 for sunitinib (FIGS. 3A-3B, 4A-4B). Again, the control eyes didn't show significant change of neovascularization during the treatment. In the eyes treated with a combination of nintedanib and mitomycin, the pterygium areas didn't increase while the saline control increased significantly (FIGS. 5A-5B). The neovascularization score didn't show significant change in this group of animal.

Example 3: Formulations

Nintedanib Ophthalmic Solution

The drug product is an isotonic ophthalmic solution prepared in 2-hydroxypropyl beta cyclodextrin or other similar cyclodextrins, and buffer solution, pH range from 5.5 to 8.0. Other viscosity, lubricant, preservative agents might be added to enhance functionality of the formulation. The compositions of the ophthalmic solution are disclosed in Table 6.

TABLE 6

Nintedanib Ophthalmic Solution

| Ingredients | Functions | Concentration Range (% w/v) |
|---|---|---|
| CBT-001 (Nintedanib free base) | Active Pharmaceutical Ingredient | 0.001-10 |

TABLE 6-continued

Nintedanib Ophthalmic Solution

| Ingredients | Functions | Concentration Range (% w/v) |
|---|---|---|
| Sodium carboxymethylcellulose | Viscosity Agent/dry eye relief | 0-1 |
| Pemulen TR | Viscosity Agent | 0-0.2 |
| Polyvinyl alcohol | Viscosity/Lubrication Agent | 0-1.5 |
| Hypromellose | Lubricant/dry eye relief | 0-1 |
| Carbomers | Lubricant/dry eye relief | 0-0.5 |
| Carmellose sodium | Lubricant/dry eye relief | 0-1 |
| Sodium hyaluronate | Lubricant/dry eye relief | 0-1.5 |
| Polyethylene glycol 400 | Lubricant/dry eye relief | 0-0.4 |
| Propylene glycol | Lubricant/dry eye relief | 0-0.6 |
| 2-hydroxypropyl beta cyclodextrin | Solubilizer | 0-10 |
| Sulfobutyl-beta-cyclodextrin | Solubilizer | 0-10 |
| Randomly methylated beta-cyclodextrin | Solubilizer | 0-5 |
| α-cyclodextrin | Solubilizer | 0-4 |
| β-cyclodextrin | Solubilizer | 0-1 |
| γ-cyclodextrin | Solubilizer | 0-1 |
| Poloxamer 188, or 237, or 407 | Solubilizer/lubricant | 0-5 |
| Polysorbate 80 | Solubilizer/lubricant/surfactant | 0-1 |
| Edetate disodium | Chelating Agent/Preservative | 0-0.01 |
| Benzalkonium chloride | Preservative | 0-0.02 |
| Sodium phosphate monobasic monohydrate | Buffer Agent | 0-0.43 |
| Sodium phosphate dibasic heptahydrate | Buffer Agent | 0-0.8 |
| Boric acid | Buffer Agent | 0-0.6 |
| Sodium borate, decahydrate | Buffer Agent | 0-0.045 |
| Citric acid, monohydrate | Buffer Agent/preservative | 0-0.13 |
| Sodium citrate, dihydrate | Buffer Agent/preservative | 0-0.45 |
| Glycerin | Tonicity Agent | 0-2.2 |
| Sodium chloride | Tonicity Agent | 0-0.83 |
| 1N Sodium hydroxide 1N Hydrochloric acid | pH Adjustment | pH 5.5-8.0 |
| Water for injection | Vehicle | Q.S. to 100 |

Nintedanib Ophthalmic Suspension

The drug product is an isotonic ophthalmic suspension prepared in carboxymethylcellulose sodium and buffer solution, pH range from 5.5 to 8.0. The drug particle sizes are reduced to below 40 micron. Other viscosity, lubricant, solubilizer, and preservative agents might be added to enhance functionality of the formulation suspension. The compositions are disclosed in Table 7.

TABLE 7

Nintedanib Ophthalmic Suspension

| Ingredients | Functions | Concentration Range (% w/v) |
|---|---|---|
| CBT-001 (Nintedanib free base) | Active Pharmaceutical Ingredient | 0.001-10 |
| Sodium carboxymethylcellulose | Viscosity Agent/dry eye relief | 0-1 |
| Pemulen TR | Viscosity Agent | 0-0.2 |
| Polyvinyl alcohol | Viscosity/Lubrication Agent | 0-1.5 |
| Hypromellose | Lubricant/dry eye relief | 0-1 |
| Carbomers | Lubricant/dry eye relief | 0-0.5 |
| Carmellose sodium | Lubricant/dry eye relief | 0-1 |
| Sodium hyaluronate | Lubricant/dry eye relief | 0-1.5 |
| Polyethylene glycol 400 | Lubricant/dry eye relief | 0-0.4 |
| Propylene glycol | Lubricant/dry eye relief | 0-0.6 |
| 2-hydroxypropyl beta cyclodextrin | Solubilizer | 0-10 |
| Sulfobutyl-beta-cyclodextrin | Solubilizer | 0-10 |
| Randomly methylated beta-cyclodextrin | Solubilizer | 0-5 |
| α-cyclodextrin | Solubilizer | 0-4 |
| β-cyclodextrin | Solubilizer | 0-1 |
| γ-cyclodextrin | Solubilizer | 0-1 |
| Poloxamer 188, or 237, or 407 | Solubilizer/lubricant | 0-5 |
| Polysorbate 80 | Solubilizer/lubricant/surfactant | 0-1 |
| Edetate disodium | Chelating Agent/Preservative | 0-0.01 |
| Benzalkonium chloride | Preservative | 0-0.02 |
| Sodium phosphate monobasic monohydrate | Buffer Agent | 0-0.43 |
| Sodium phosphate dibasic heptahydrate | Buffer Agent | 0-0.8 |
| Boric acid | Buffer Agent | 0-0.6 |
| Sodium borate, decahydrate | Buffer Agent | 0-0.045 |
| Citric acid, monohydrate | Buffer Agent/preservative | 0-0.13 |
| Sodium citrate, dihydrate | Buffer Agent/preservative | 0-0.45 |
| Glycerin | Tonicity Agent | 0-2.2 |
| Sodium chloride | Tonicity Agent | 0-0.83 |
| 1N Sodium hydroxide 1N Hydrochloric acid | pH Adjustment | pH 5.5-8.0 |
| Water for injection | Vehicle | Q.S. to 100 |

Nintedanib Ophthalmic Emulsion

The drug product is an isotonic ophthalmic emulsion. The drug is dissolved in the mixture oil phase and emulsifier excipients which is then emulsified and mixed with an aqueous phase with pH range from 5.5 to 8.0. Other viscosity, lubricant, solubilizer, and preservative agents might be added to enhance functionality of the emulsion formulation. The compositions are disclosed in Table 8.

TABLE 8

Nintedanib Ophthalmic Emulsion

| Ingredients | Functions | Concentration (% w/w) |
|---|---|---|
| CBT-001 (Nintedanib free base) | Active Pharmaceutical Ingredient | 0.001-10 |
| Castor oil | Oil solvent | 0-1.25 |
| Polyoxyl-40-Stearate | Emulsifier | 0-0.25 |
| Polysorbate 80 | Solubilizer/Emulsifier/Surfactant | 0-1 |
| Sulfobutyl-β-cyclodextrin | Solubilizer | 0-5 |
| 2-Hydroxypropyl-beta-cyclodextrin | Solubilizer | 0-5 |
| Randomly methylated beta-cyclodextrin | Solubilizer | 0-5 |
| α-cyclodextrin | Solubilizer | 0-4 |
| β-cyclodextrin | Solubilizer | 0-1 |
| γ-cyclodextrin | Solubilizer | 0-1 |
| Glycerin | Tonicity Agent | 0-2.2 |
| Sodium Chloride | Tonicity Agent | 0-0.83 |
| Pemulen TR2 | Viscosity Agent | 0-0.1 |
| Sodium carboxymethylcellulose | Viscosity Agent | 0-0.5 |
| Polyvinyl alcohol | Viscosity/Lubrication Agent | 0-1.5 |
| Hypromellose | Lubricant/dry eye relief | 0-1 |
| Carbomers | Lubricant/dry eye relief | 0-0.5 |

TABLE 8-continued

Nintedanib Ophthalmic Emulsion

| Ingredients | Functions | Concentration (% w/w) |
|---|---|---|
| Carmellose sodium | Lubricant/dry eye relief | 0-1 |
| Sodium hyaluronate | Lubricant/dry eye relief | 0-1.5 |
| Polyethylene glycol 400 | Lubricant/dry eye relief | 0-0.4 |
| Propylene glycol | Lubricant/dry eye relief | 0-0.6 |
| Poloxamer 188, or 237, or 407 | Solubilizer/lubricant | 0-5 |
| Boric acid | Buffer | 0-0.6 |
| Sodium borate, decahydrate | Buffer | 0-0.045 |
| Citric acid, monohydrate | Buffer/preservative | 0-0.13 |
| Sodium citrate, dihydrate | Buffer/preservative | 0-0.45 |
| Sodium phosphate, monobasic monohydrate | Buffer | 0-0.43 |
| Sodium phosphate dibasic heptahydrate | Buffer | 0-0.8 |
| 1N & 5N Sodium hydroxide 1N Hydrochloric acid | pH Adjustment | pH 5.5-8.0 |
| Water for injection | Aqueous Vehicle | Q.S. 100 |

Nintedanib Sustained Release Semi-Solid Formulation

The drug product is an isotonic sustained release semi-solid formulation. The drug is dissolved and/or suspended in a semi-solid medium with pH range from 5.5 to 8.0. Other viscosity, lubricant, solubilizer, and preservative agents might be added to enhance functionality of the sustained release semi-solid formulation. The compositions are disclosed in Table 9.

TABLE 9

Sustained Release Semi-Solid Formulation

| Ingredients | Functions | Concentration (% w/w) |
|---|---|---|
| CBT-001 (Nintedanib free base) | Active Pharmaceutical Ingredient | 0.001-10 |
| Xanthan Gum | Viscosity/Thickener | 0-10 |
| Hydroxypropyl methylcellulose | Viscosity/Thickener | 0-10 |
| Sodium hyaluronate | Viscosity/Thickener | 0-5 |
| Hyaluronic acid | Viscosity/Thickener | 0-5 |
| Boric acid | Buffer | 0-0.6 |
| Sodium borate, decahydrate | Buffer | 0-0.045 |
| Citric acid, monohydrate | Buffer/preservative | 0-0.13 |
| Sodium citrate, dihydrate | Buffer/preservative | 0-0.45 |
| Sodium phosphate, monobasic monohydrate | Buffer | 0-0.43 |
| Sodium phosphate dibasic heptahydrate | Buffer | 0-0.8 |
| 1N & 5N Sodium hydroxide 1N Hydrochloric acid | pH Adjustment | pH 5.5-8.0 |
| Water for injection | Aqueous Vehicle | Q.S. 100 |

Nintedanib Sustained Release Implants

The drug product is a solid implant. The drug is mixed and blended with one or more polymers. The mixture of drug and polymers is melted at a predetermined temperature and extruded into a filament with a predetermined diameter size. The formulation filament is cut into a predetermined size of segment which can be implanted into ocular tissues. The compositions are disclosed in Table 10.

TABLE 10

Sustained Release Implants

| Ingredients | Functions | Concentration (% w/w) |
|---|---|---|
| CBT-001 (Nintedanib free base) | Active Pharmaceutical Ingredient | 0.001-10 |
| Poly (D,L-Lactide), i.v. 0.25-0.35 dL/g | Polymer | 0-100 |
| Poly (D,L-Lactide-coglycolide) i.v. 0.14-0.22 dL/g | Polymer | 0-100 |
| Poly (D,L-Lactide), i.v. 0.16-0.25 dL/g | Polymer | 0-100 |
| Polyethylene Glycol 3350 | Polymer | 0-20 |
| Resomer ®RG755S | Polymer | 0-100 |
| Resomer ®RG753H | Polymer | 0-100 |

Without limitation, an example composition, for use in the methods according to the invention, may be modified from existing ophthalmically acceptable compositions.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating pterygium in an eye of a subject, comprising administering to the affected eye of the subject a therapeutically effective amount of nintedanib.

2. The method of claim 1, wherein treating pterygium comprises reducing hyperemia, regressing a pterygium, or stabilizing a pterygium.

3. The method of claim 2, wherein treating pterygium comprises reducing hyperemia.

4. The method of claim 2, wherein treating pterygium comprises pterygium regression.

5. The method of claim 2, wherein treating pterygium comprises pterygium stabilization.

6. The method of claim 2, wherein treating pterygium further comprises reducing a symptom of pterygium.

7. The method of claim 6, wherein the symptom of pterygium comprises ocular discomfort, irritation, blurred vision, foreign body sensation, or pain.

8. The method of claim 6, wherein the symptom of pterygium is a clinical symptom or a subclinical symptom.

9. The method of claim 1, wherein the nintedanib is administered to the affected eye in the form of a topical ocular formulation or an ocular implant.

10. The method of claim 9, wherein the topical ocular formulation is a solution or a suspension.

11. The method of claim 9, wherein the topical ocular formulation further comprises one or more pharmaceutically acceptable excipients.

12. The method of claim 9, wherein the ocular implant is injected into the affected eye.

13. The method of claim 9, wherein the ocular implant further comprises one or more pharmaceutically acceptable excipients.

14. The method of claim 1, further comprising administering to the affected eye of the subject a pharmaceutically effective amount of an antimetabolite.

15. The method of claim 14, wherein the antimetabolite blocks epithelial and fibroblast cell proliferation.

16. The method of claim 14, wherein the antimetabolite is selected from the group consisting of mitomycin C, 5-fluorouracil, and thiotepa.

17. The method of claim 1, wherein the administration is performed prior to surgical removal of a pterygium.

18. The method of claim 1, wherein the administration is performed during a surgical procedure to remove a pterygium.

19. The method of claim 1, wherein the administration is performed following surgical removal of a pterygium.

* * * * *